United States Patent
Russo

(10) Patent No.: US 11,383,026 B2
(45) Date of Patent: Jul. 12, 2022

(54) WEARABLE INJECTOR

(71) Applicant: SYNOLUS MEDICAL, INC., Gettysburg, PA (US)

(72) Inventor: Robert Scott Russo, Gettysburg, PA (US)

(73) Assignee: Synolus Medical, Inc., Gettysburg, PA (US)

( * ) Notice: Subject to any disclaimer, the term of this patent is extended or adjusted under 35 U.S.C. 154(b) by 0 days.

(21) Appl. No.: 17/604,781

(22) PCT Filed: Jan. 8, 2020

(86) PCT No.: PCT/US2020/012751
§ 371 (c)(1),
(2) Date: Oct. 19, 2021

(87) PCT Pub. No.: WO2020/219127
PCT Pub. Date: Oct. 29, 2020

(65) Prior Publication Data
US 2022/0143303 A1    May 12, 2022

(51) Int. Cl.
*A61M 5/142* (2006.01)
*A61M 5/172* (2006.01)
*A61M 5/44* (2006.01)
A61M 5/14 (2006.01)

(52) U.S. Cl.
CPC .... *A61M 5/14232* (2013.01); *A61M 5/14248* (2013.01); *A61M 5/445* (2013.01); *A61M 2005/1402* (2013.01); *A61M 2005/14252* (2013.01); *A61M 2205/215* (2013.01); *A61M 2205/3368* (2013.01)

(58) Field of Classification Search
CPC .......... A61M 2005/1402; A61M 2005/14208; A61M 5/14232; A61M 5/14248; A61M 5/445; A61M 2005/14252; A61M 2205/215; A61M 2205/3368
See application file for complete search history.

(56) References Cited

U.S. PATENT DOCUMENTS

| | | | |
|---|---|---|---|
| 7,744,589 B2* | 6/2010 | Mounce | A61M 5/14248 604/890.1 |
| 8,435,209 B2* | 5/2013 | Hanson | A61M 5/1413 604/67 |
| 9,039,659 B2* | 5/2015 | Hanson | A61M 5/14248 324/207.21 |
| 9,220,838 B2 | 12/2015 | Soma et al. | |

(Continued)

FOREIGN PATENT DOCUMENTS

| | | |
|---|---|---|
| EP | 2762183 A1 | 8/2014 |
| WO | 2019008529 A1 | 1/2019 |

OTHER PUBLICATIONS

Korean Patent Office, International Search Report in corresponding PCT/US2020/12751, dated May 29, 2020, 4 pages.

(Continued)

*Primary Examiner* — Quynh-Nhu H. Vu
(74) *Attorney, Agent, or Firm* — Hooker & Habib, P.C.

(57) ABSTRACT

A wearable injector for automated delivery of biologic drugs that solves the problem of high volume and high viscosity drug administration by providing a device that can be worn by the patient through use of an adhesive patch to deliver the medication slowly over extended periods of time.

39 Claims, 20 Drawing Sheets

(56) References Cited

U.S. PATENT DOCUMENTS

| | | |
|---|---|---|
| 9,724,462 B2 | 8/2017 | Rotem |
| 9,878,091 B2 | 1/2018 | Cabiri |
| 10,420,508 B2* | 9/2019 | Antonio ............. A61B 5/14532 |
| 10,463,572 B2 | 11/2019 | Shor et al. |
| 10,463,787 B2 | 11/2019 | Shor et al. |
| 2010/0137790 A1* | 6/2010 | Yodfat .............. A61M 5/14248 |
| | | 604/67 |
| 2014/0088508 A1 | 3/2014 | Ryan et al. |
| 2015/0265780 A1 | 9/2015 | Pesach et al. |
| 2019/0015585 A1 | 1/2019 | Smith |
| 2020/0214625 A1* | 7/2020 | Hooven .................. A61M 5/31 |

OTHER PUBLICATIONS

Korean Patent Office, Written Opinion of the International Searching Authority in corresponding PCT/US2020/12751, dated May 29, 2020, 4 pages.

* cited by examiner

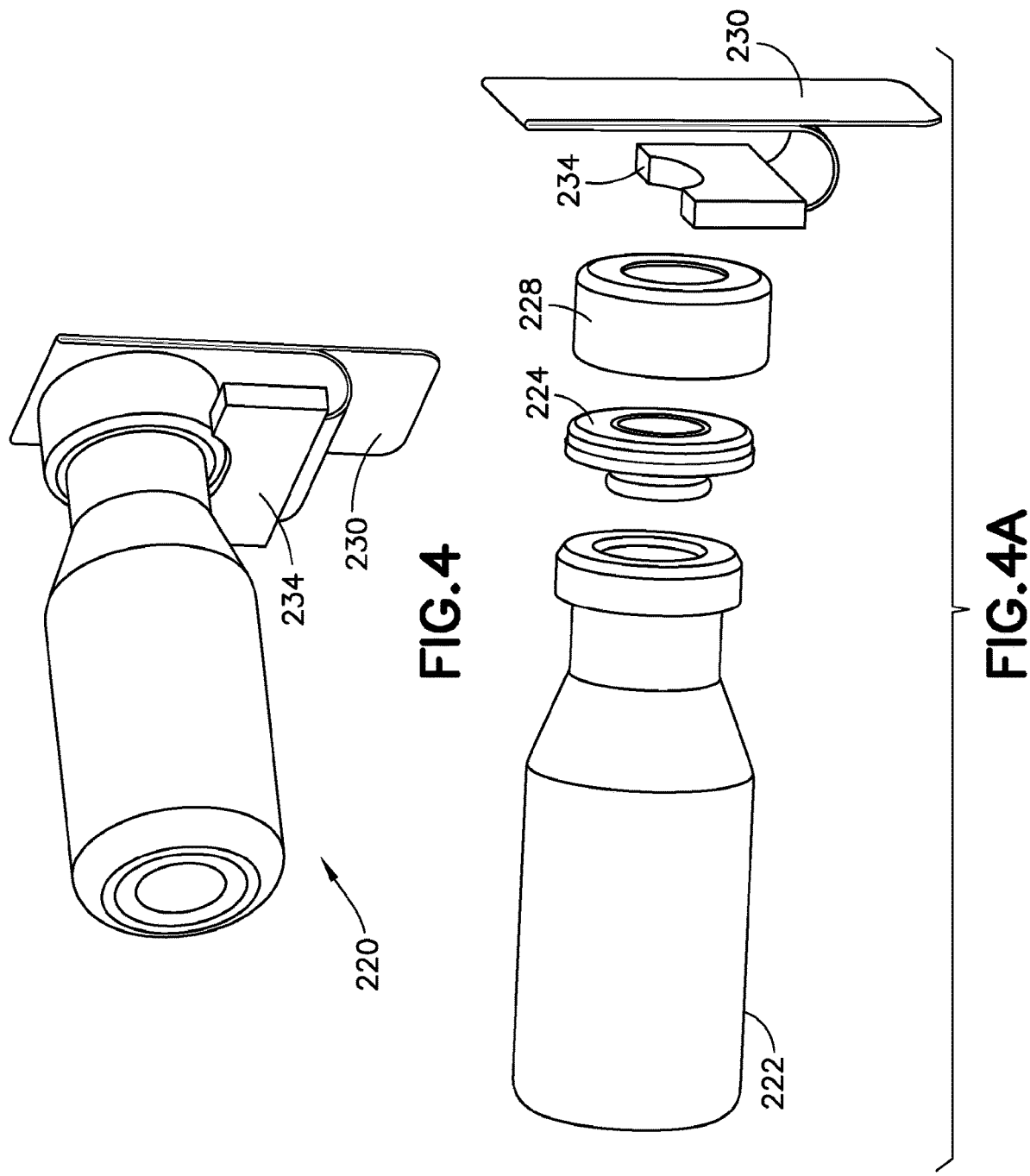

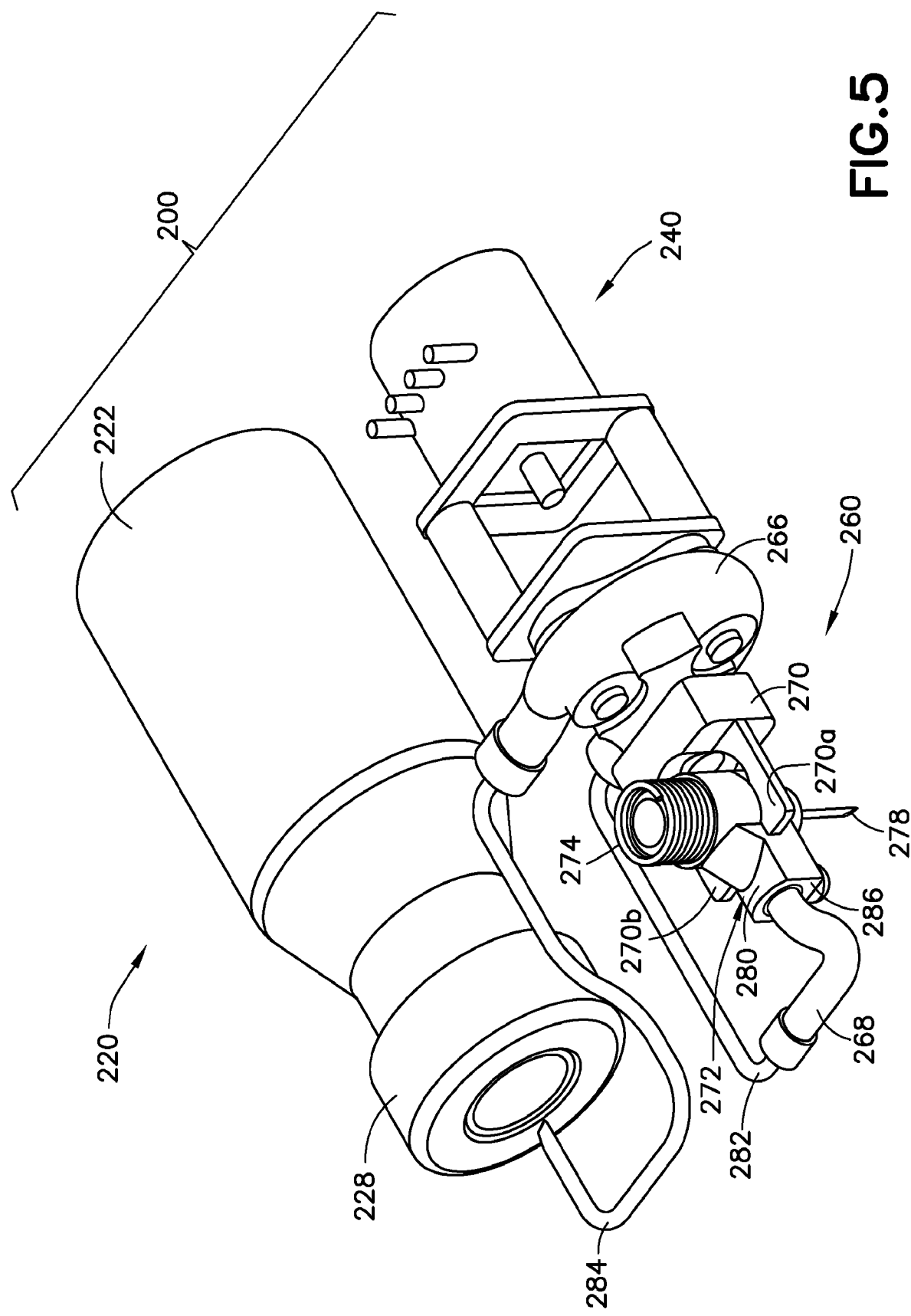

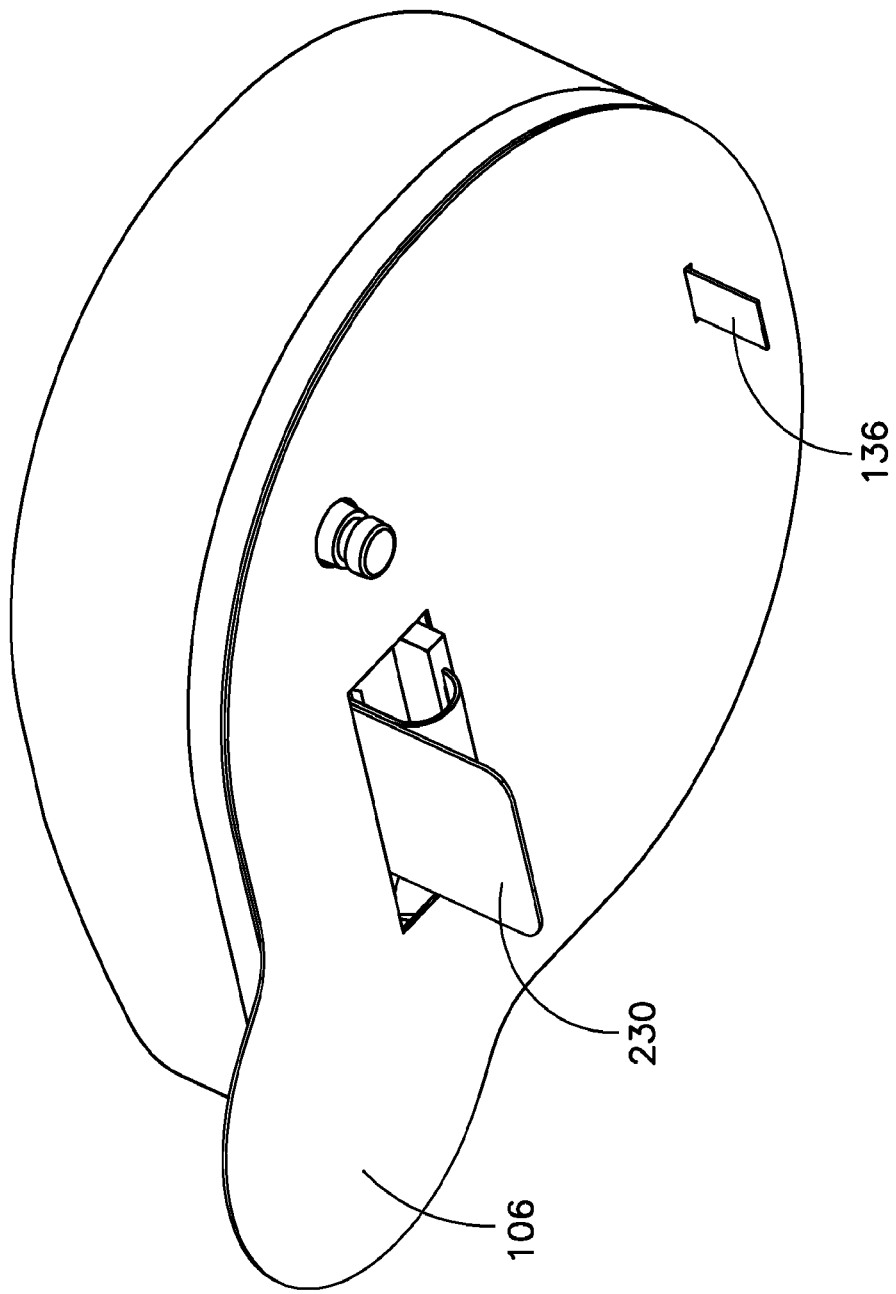

WEARABLE INJECTOR

FIELD OF THE INVENTION

The present invention is directed to a wearable injector.

BACKGROUND OF THE INVENTION

Biologic drugs continue to increase in their use to treat a variety of conditions such as autoimmune diseases such as Rheumatoid Arthritis (RA), Lupus, and Multiple Sclerosis (MS), cancers including lung cancer, breast cancer, leukemia and more, various cardiovascular diseases, and more. The most common type of biologic drug, monoclonal antibodies (mAbs) have increased in their use exponentially in recent years. Over 50% of the total 73 mAbs ever approved for use on patients were launched within the last 5 years. In 2017, a record 10 new mAb drugs were introduced. Their revolutionary trend shows no signs of slowing down, with near 7,000 new biologic drugs currently in development, with most of these pipeline drugs requiring doses of greater than 1 mL of a viscous solution. Due to their greater volume and higher viscosity, traditional syringes or autoinjectors are not feasible or practical to deliver these medications. This presents a problem for pharmaceutical companies developing the drugs of having no good solution to get the drug into patients beyond the clinical setting.

A first problem is that syringes and autoinjectors are not suitable for many biologic medications/drugs, i.e., biologics. These drugs are typically injected. Most of the 7000 biologic drugs in the current development pipeline are high volume dosage drugs (>1 ml). Biologics also can be highly viscous requiring excessive plunger force to dispense the drug through the injection needle within the relatively short injection time associated with the use of syringe or autoinjectors. The larger injection volumes and/or higher viscosity of the drug causes for syringes and autoinjectors to no longer meet the delivery needs of many biologic drugs.

A second problem is that cartridge- or syringe-based delivery devices introduce new factors to the drug-device development process creating additional challenges which must be overcome prior to moving forward with combination product commercialization. The traditional approach followed by biopharmaceutical companies is to use and/or develop high-volume cartridge- or syringe-based injection devices as the configuration for patient use beyond the clinical setting. Such devices require use of a rubber plunger and silicone oil lubricant which are in long term contact with the drug during product storage. For biologic drugs, these additional drug-contacting materials can introduce drug stability issues (i.e., drug degradation problems). Before the commercial application delivery device is adopted, biologic drugs are stored and developed in standard glass vials. Such containers involve no silicone oil lubricant or rubber plungers. Switching from the vial container into a cartridge or syringe container increases risk, as storing the newly developed drug in a different container may prove problematic. Additionally, new processes for washing, lubricating, sterilizing, and filling the different containers must be developed and implemented adding risk, time, and financial resources to development programs.

It is thus desirable to ensure that patients with chronic diseases have access to life changing drugs as early as possible by minimizing the drug development and regulatory approval timelines while also ensuring maximum patient compliance while on drug therapy. Several highly effective drugs for chronic diseases do not make it to market today as they are not formulated to fit in traditional drug delivery devices such as syringes or autoinjectors. With the rise in biologics, proteins and peptides, many drugs are highly viscous or have large delivery volumes making patient self-injection impractical or impossible. Delivery of these types of drugs therefore requires some form of a wearable injection system, which has created the unmet need in the marketplace. While some new wearable injector devices have entered the market, they all require cumbersome, time-consuming, and require error-prone steps to be performed by the user, drastically minimizing compliance. Addressing these two concerns of maximizing the likelihood of commercializing a drug (and doing so rapidly) while simultaneously enhancing patient compliance reduces the overall burden of healthcare costs on society and the economy by ensuring patients get access to drugs that would otherwise have not made it to market merely due to the absence of a suitable delivery mechanism. The need for better delivery devices is driven by factors such as, an increase in prevalence of chronic diseases (autoimmune diseases, cancers, etc.) due to increasing lifespan, a rise of biologics, proteins, peptides to treat these chronic diseases, and strong competition across pharma/biotech companies where competing drugs have similar dosing regimens and side effects thereby leading to the injection device becoming the differentiator and competitive advantage. Moreover, as more and more blockbuster drugs come off patent, the drug delivery device once again becomes the differentiator in competing against generics or biosimilars and preserving market share. Patient care is moving towards homecare with self-care/self-injection becoming common place. As patients become more educated and informed, the patient is viewed as the consumer and will ultimately be a key decision maker in his/her treatment regimens. As a result, a convenient drug delivery device is paramount.

SUMMARY OF THE INVENTION

The present invention is directed to a fully integrated wearable injector for automated delivery of biologic drugs. The inventive injector solves the problem of high volume and high viscosity drug administration by providing a device that can be worn by the patient through use of an adhesive patch to deliver the medication slowly over extended periods of time. Certain advantages of the inventive injector differentiate it from other injectors, including, by way of illustration and not limitation: 1) its pre-filled and pre-assembled format improving acceptance and adoption; 2) its vial-based design eliminates the need to switch drug storage into syringe or other custom container in late stage clinical trials avoiding additional drug stability studies, accelerating commercialization and reducing risks; and 3) it provides important flexibility through clinical trials as doses, injection rates, injected volumes can change. Standard vials are also the ideal container for drug protection and stability. At least part of the innovation of the inventive injector is its novel design and engineering solutions which solve technical problems associated with an integrated vial approach for direct and automatic injection. This innovation greatly simplifies use for patients and makes adoption easier for pharmaceutical companies as it saves time in development and reduces commercialization cost.

The inventive injector may be used by pharmaceutical, biopharmaceutical, and similar companies that develop and manufacture biologic drugs. The inventive injector provides these companies with a solution for introducing/launching high volume and high viscosity drugs to market. The inventive injector is expected to accelerate the adoption of wearable injectors for broad impact in making treatment easier and more convenient for patients while reducing costs and increasing treatment accessibility.

The innovation of the present invention lies in its novel design which enables differentiating features such as its pre-filled and pre-assembled format making it simple and reliable for at home self-injection. Use of a standard glass vial, the most common, easiest to fill, and most compatible container for storage of biologic drugs, offers significant development and commercialization advantages for pharmaceutical companies.

The injector of the present invention provides a solution for administration of therapeutic drugs when dosage volumes and drug viscosity make use of a syringe or autoinjectors not possible or impractical. Additionally, when a given therapy could be administered at an infusion clinic, the present invention provides an alternative to this approach that enables the infusions to take place within the comfort of the patient's home. This translates to greater convenience for the patient, reduced cost to the healthcare system, and significantly increases the likelihood of patient compliance. Infusion clinics can also have limited capacity to provide treatment and in more remote parts of the world access to a clinic may not be available at all. The present invention can enable patients to receive medication that may otherwise not be accessible to them.

In accordance with embodiments of the present invention, a wearable injector is provided having a number of features and advantages not currently found in available devices. The inventive injector uses a standard vial, which leads to significant commercialization advantages, including transitioning from clinical to commercial device without the need for additional drug stability studies, saving time, money, and resources, using the most economical and widely available filling equipment (vial filling), accelerating advancement through clinical trials and simplifying commercial scale production, eliminating need for silicone oil lubricant (required for syringes, other non-vial containers) which can lead to protein aggregation, degrading the drug, eliminating the need for silicone oil lubricant avoiding need for specialized washing and siliconization equipment, eliminating the need for silicone oil lubricant enabling simpler sterilization processes to be used (e.g., steam auto-clave) for primary container sterilization over more complex and expensive methods such as ethylene oxide sterilization, eliminating the need for rubber plungers to expel the drug from a container reducing number of required components, simplifying commercialization, and eliminating the need for rubber plungers to expel the drug from a container avoiding any problems that could arise with drug contact with said rubber plungers during storage.

The inventive injector is pre-filled and pre-assembled, which makes device easier to use for patients as no filling of device or installation of drug container before use is required and reduces risk of user error increasing compliance to treatment.

The inventive injector is software configurable and controllable to accommodate high viscosity, variable dose volume, and variable rate control, which enables a single device configuration to work with many biologics that all have different viscosity, dose volume, and injection rate needs, and provides the flexibility needed to address changes in efficacious dose and target injection rate without the need to customize system hardware.

The inventive injector can warm drugs prior to injection reducing pain or discomfort or occurrence of injection site reaction, which can occur when the drug is injected cold. The warming is monitored such that the timing of injection onset can be informed by the drug temperature to provide benefit to the patient and/or device functionality, for example, permitting injection only after the drug has warmed to pre-determined temperature to ensure the patient realizes the benefit, and permitting injection only after the drug has warmed to a pre-determined temperature to ease mechanical stress on the pump mechanisms as warming of the drug reduces and stabilizes fluid viscosity.

The injector of the present invention further possesses the capability to deliver variable volumes of viscous solutions, on the order of 1 mL-10 mL with viscosity levels anywhere between 1 and 100 cP, or higher depending on delivery time limitations. In addition, the inventive injector possesses electro-mechanical mechanisms for automatic fluid extraction from the vial and injection into subcutaneous tissue; variable delivery rates achieved through software changes only.

An embodiment of the present invention is directed to a wearable injector for delivering a drug into a body part of a patient comprising, a housing, a base connected with the housing and releasably securable on the body part of the patient, a carrier rotatably arranged within the housing and base, and a delivery system on the carrier. The delivery system comprises a container sub-assembly for containing the drug, a drive control sub-assembly coupled with the container sub-assembly and configured for controlling delivery of the drug into the patient, a flow-path sub-assembly providing a fluid path with the container sub-assembly via which a fluid can be introduced into the container sub-assembly and via which the drug can be extracted from the container sub-assembly, wherein the drive control sub-assembly engages the flow-path sub-assembly to cause the fluid to be introduced into the container sub-assembly and to cause the drug to be extracted from the container and delivered into the patient, a sensor for detecting one of temperature of the body part, temperature of the drug in the container sub-assembly, and orientation of the container sub-assembly, and a controller receiving an input from the sensor and controlling the drive control sub-assembly based upon the input to set a state of the injector.

In a further embodiment of the present invention the drive control sub-assembly further comprises a peristaltic pump.

In a further embodiment of the present invention the peristaltic pump further comprises a drive motor and a pump wheel controllable by the drive motor.

In a further embodiment of the present invention the controller receives power from a power source and wherein the container sub-assembly further comprises a container for containing the drug, wherein the controller activates the drive control sub-assembly to pressurize the container when the controller receives power from the power source.

In a further embodiment of the present invention the controller activates the drive control sub-assembly to introduce air into the container via the flow-path sub-assembly when the controller receives power from the power source.

In a further embodiment of the present invention the controller activates the drive control sub-assembly to introduce a predetermined amount of air into the container.

In a further embodiment of the present invention the predetermined amount of air is based upon one of the volume of drug to be dispensed and the viscosity of the drug.

In a further embodiment of the present invention the container sub-assembly further comprises a container, and wherein the flow-path sub-assembly defines a fluid path with the container, wherein the drive control sub-assembly causes the injector to be primed by causing air to travel along the fluid path into the container, and wherein the drive control sub-assembly causes the injector to be extracted from the container for delivery into the patient by causing the drug to travel along the fluid path out of the container.

In a further embodiment of the present invention the drive control sub-assembly causes the fluid path to be primed with the drug prior to delivery of the drug into the patient.

In a further embodiment of the present invention the container sub-assembly further comprises a container, and wherein the flow-path sub-assembly defines a fluid path with the container, wherein the drive control sub-assembly causes the injector to be primed by causing air to travel along the fluid path into the container.

In a further embodiment of the present invention the flow-path sub-assembly further comprises an injection needle connected with the fluid path for delivering the drug into the patient, and wherein the drive control sub-assembly causes the drug to travel along the fluid path and through the injection needle into the patient when the injector is primed.

In a further embodiment of the present invention a bearing between the carrier and housing at least partially enables rotation of the carrier within the housing.

In a further embodiment of the present invention the bearing comprises at least one roller disposed in a recess defined in one of the carrier and housing, the roller being freely rotatable in the recess.

In a further embodiment of the present invention an adhesive on a part of the base releasably secures the base on the body part of the patient.

In a further embodiment of the present invention the adhesive comprises an annulus or partial annulus on a part of the base.

In a further embodiment of the present invention the container sub-assembly further comprises a container for the drug, and wherein the sensor further comprises an orientation sensor configured to determine an orientation of the container, the controller setting a state of the injector based up the orientation of the container.

In a further embodiment of the present invention the state of the injector comprises one of an injection state and a non-injection state, and wherein the controller is configured to toggle the state of the injector to/from the injection state from/to the non-injection state based upon an output from the orientation sensor.

In a further embodiment of the present invention the container sub-assembly further comprises a container for the drug, and wherein the sensor further comprises a first temperature sensor configured to determine a temperature of the drug in the container, wherein the controller is configured to control the drive control sub-assembly to cause the drug to be delivered into the patient when the temperature of the drug in the container is at least at a predetermined temperature.

In a further embodiment of the present invention the predetermined temperature is at least 60° F.

In a further embodiment of the present invention the container sub-assembly further comprises a container for the drug, and wherein the sensor further comprises a second temperature sensor configured to determine whether the injector is on the patient's body.

In a further embodiment of the present invention the second temperature sensor is configured to determine a temperate of the patient at or near the body part, wherein the controller is configured to control the drive control sub-assembly to cause the drug to be delivered into the patient when the temperature of the patient at or near the body part is at least at a predetermined temperature.

In a further embodiment of the present invention the predetermined temperature is at least within 5° F. of 98.6° F.

In a further embodiment of the present invention a lock prevents rotation of the carrier.

In a further embodiment of the present invention the flow-path sub-assembly further comprises an injection needle assembly comprising a needle carrier, an injection needle, and a needle position nub, and wherein the base further comprises at least one recess for receiving the needle position nub, wherein the injection needle assembly is movable from a first position in which the needle position nub and recess are in spaced apart relation to each other, and a second position in which the needle position nub is in the recess thereby preventing rotation of the carrier.

In a further embodiment of the present invention the container sub-assembly further comprises a container for containing the drug, the container having a pierceable seal, and wherein the flow-path sub-assembly further comprises a fluid path having a needle, the injector further comprising a spring for causing the container to move in a predetermined direction, and a removable barrier located between the pierceable seal and the needle maintain each in a sterile condition, wherein removal of the removable barrier causes the spring to cause the container to move in the predetermined direction in which the needle pierces the pierceable seal.

In a further embodiment of the present invention the injector is contained in a disposable package openable by a user of the injector, wherein the removable barrier is removed coincident with a user opening the package.

In a further embodiment of the present invention a collar is provided on the container and a container activator, wherein the spring engages the container activator to engage the collar to cause the container to move in a predetermined direction in which the needle pierces the pierceable seal.

In a further embodiment of the present invention a power source powers the injector, and a pull-tab that, when pulled enables the power source to power the injector.

In a further embodiment of the present invention the container sub-assembly further comprises a container for containing the drug, and wherein the drive control sub-assembly further comprises a pump operable to pressurize the container, and operable to cause the drug to flow from the container, upon the container being pressurized by the pump to a predetermined level, the pump automatically causes the drug to flow from the container.

In a further embodiment of the present invention an audible and/or visual indicator indicates a state of the injector.

In a further embodiment of the present invention the state is one of orientation and operational state of the injector In a further embodiment of the present invention a push-button is provided for user activation of the injector.

In a further embodiment of the present invention a needle is provided for delivering the drug into the patient, and wherein the container sub-assembly further comprises a container having a preferred orientation, wherein the carrier is configured to automatically orient the container in the preferred orientation, and wherein the injector is configured to automatically cause the needle to be inserted into the body part of the patient when the container is in the preferred orientation.

In a further embodiment of the present invention a needle is provided for delivering the drug into the patient and a user-depressible push-button, and wherein the container sub-assembly further comprises a container having a preferred orientation, wherein the carrier is configured to orient the container in the preferred orientation upon user first depression of the push-button, and wherein the injector is configured to cause the needle to be inserted into the body part of the patient when the container is in the preferred orientation upon user subsequent depression of the push-button.

In a further embodiment of the present invention the container sub-assembly further comprises a container having a preferred orientation, the injector further comprising a needle for delivering the drug into the patient and orientation means for changing the orientation of the container, wherein the container orientation is set by user use of the orientation means, and wherein the injector is configured to automatically cause the needle to be inserted into the body part of the patient when the container is in the preferred orientation by user use of the orientation means.

In a further embodiment of the present invention the orientation means comprises a tab connected with the carrier and that enables a user to cause the carrier to rotate within the housing.

In a further embodiment of the present invention a needle is provided for delivering the drug into the patient, orientation means for changing the orientation of the container, and a user-depressible push-button, wherein the container sub-assembly further comprises a container having a preferred orientation, wherein the container orientation is set by user use of the orientation means subsequent to user first depression of the push-button, and wherein the injector is configured to cause the needle to be inserted into the body part of the patient when the container is in the preferred orientation upon user subsequent depression of the push-button.

In a further embodiment of the present invention the orientation means comprises a tab connected with the carrier and that enables a user to cause the carrier to rotate within the housing.

Another embodiment of the present invention is directed to a method for operating a wearable injector comprising a housing, a base connected with the housing and releasably securable on the body part of the patient, a carrier rotatably arranged within the housing and base, and a delivery system on the carrier comprising a container sub-assembly for containing the drug, a drive control sub-assembly coupled with the container sub-assembly and configured for controlling delivery of the drug into the patient, a flow-path sub-assembly providing a fluid path with the container sub-assembly via which a fluid can be introduced into the container sub-assembly and via which the drug can be extracted from the container sub-assembly, a sensor for detecting one of temperature of the body part, temperature of the drug in the container sub-assembly, and orientation of the container sub-assembly, and a controller receiving an input from the sensor. The method comprises the step of causing the drive control sub-assembly to engage the flow-path sub-assembly to cause the fluid to be introduced into the container sub-assembly and to cause the drug to be extracted from the container and delivered into the patient based upon the input from the sensor to set a state of the injector.

DESCRIPTION OF THE DRAWINGS

Embodiments of the present invention will now be described with reference to the following FIGS. wherein:

FIG. 5 depicts a delivery system including a vial container sub-assembly (VCSA), a flow path sub-assembly (FSA), and a drive control sub-assembly (DCSA) in accordance with embodiments of the present invention;

FIGS. 9A-9C depict views of a wearable injector in accordance with embodiments of the present invention in a stored or pre-use state;

DETAILED DESCRIPTION OF THE INVENTION

The present invention is directed to a fully integrated automated wearable injector for at home self-administration of drugs. The inventive injector includes a controller to control certain functions and aspects of the injector, effectively making the inventive injector a smart device. Advantageously, the inventive injector utilizes a standard glass vial as its primary container, an innovative aspect of which is that it enables differentiating features such as its pre-filled and pre-assembled format making it simple and reliable for at home self-injection. Use of a standard glass vial, the most common, easiest to fill, and most compatible container for storage of biologic drugs, offers significant development and commercialization advantages.

Figure 1A:
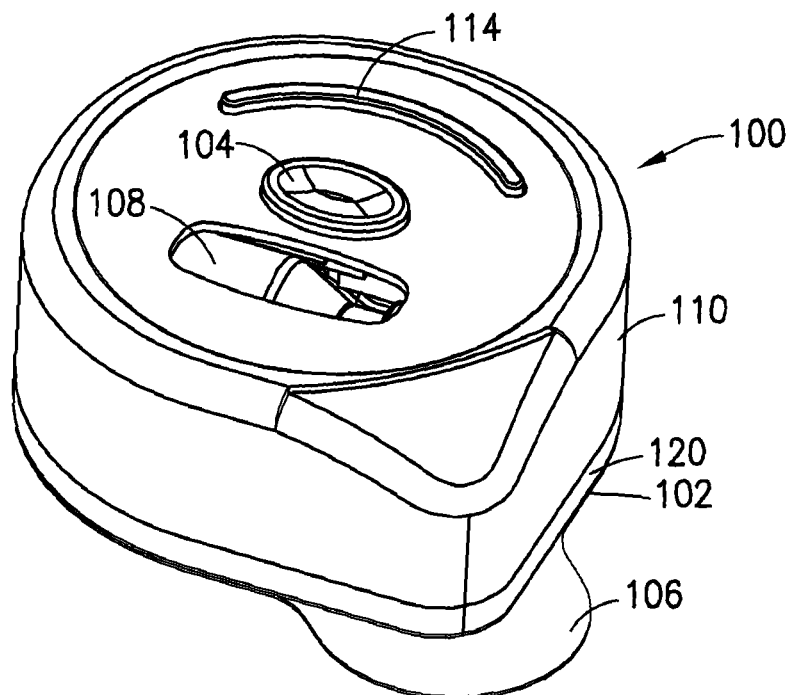
FIGS. 1A-1D depict perspective top views of a wearable injector in accordance with embodiments of the present invention.
Figure 1B:
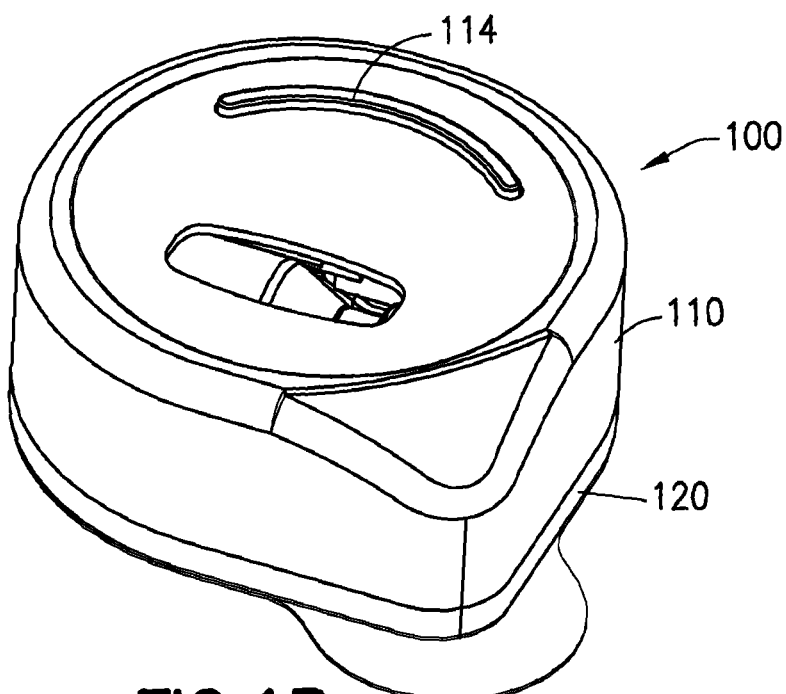
Figure 1C:
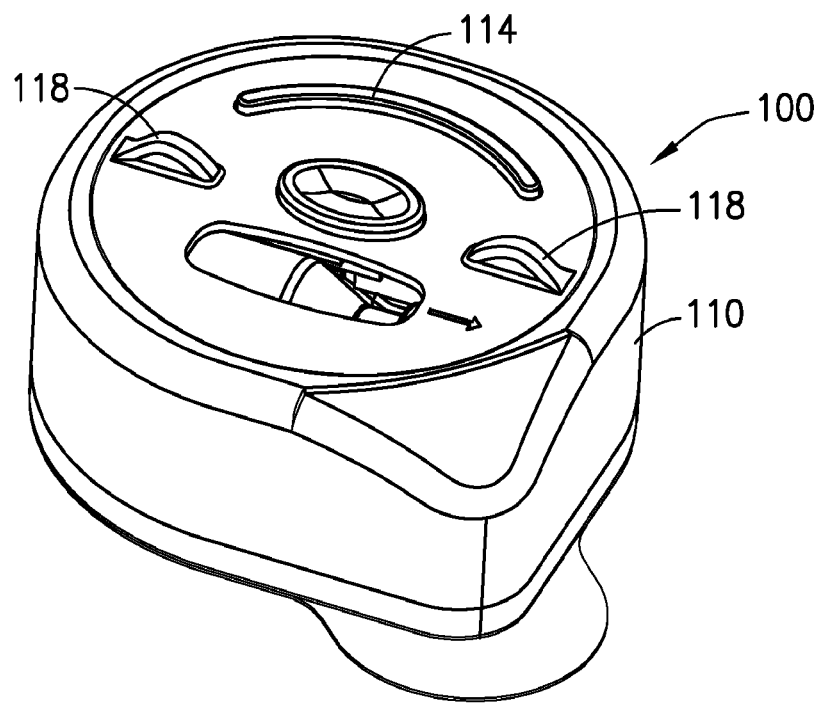
Figure 1D:
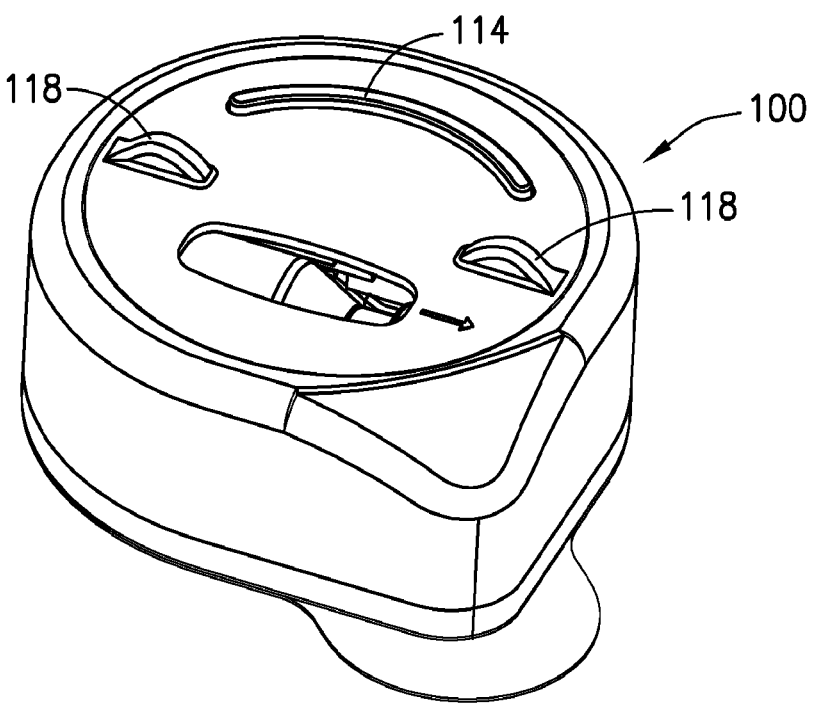

With reference next to the drawings, and in particular FIGS. 1A-1D and 2, the present invention will now be discussed in detail. A first embodiment of the wearable injector 100 of the present invention is depicted in FIG. 1A and is an auto-orienting, user-activated device. A second embodiment of the wearable injector 100 of the present invention is depicted in FIG. 1B and is an auto-orienting, auto-activated device. A third embodiment of the wearable injector 100 of the present invention is depicted in FIG. 1C and is a user-orienting, user-activated device. A fourth embodiment of the wearable injector 100 of the present invention is depicted in FIG. 1D and is a user-orienting, auto-activated device. Each of these embodiments will be discussed in greater detail below.

Figure 2:
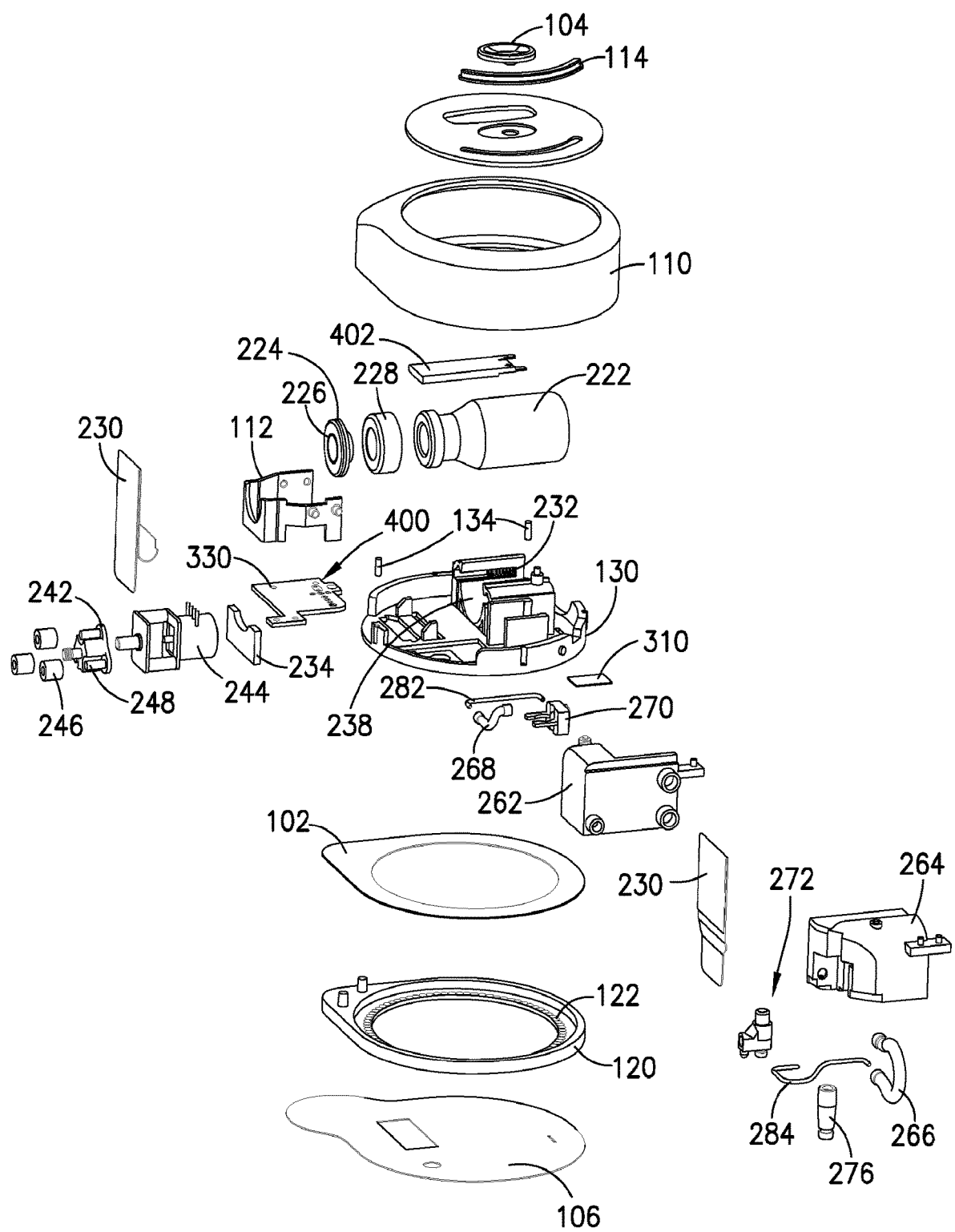
FIG. 2 depicts an exploded view of a wearable injector in accordance with embodiments of the present invention.

The inventive injector 100 is depicted in exploded view in FIG. 2 and comprises a housing 110 and a base 120 that connect together and contain the other components of the injector 100. A window 108 defined in the injector 100 enables a user of the injector 100 to see the container 222 and its contents. A delivery system carrier 130 is disposed within the housing 110 and on the base 120 and is rotatable with respect to both either by the user and one or more position tabs 118 on the housing cap 144 or, alternatively, the delivery system carrier 130 may self-orient by appropriately designed and placed mass within the injector 100. In any case, a visual and/or audible indicator will indicate to the user when the injector 100 is properly orientated on the patient's body. Rotation of the carrier 130 while the housing 110 and base 120 remain fixed enables proper orientation of the container 222 for delivery of a drug 290 contained in the container 222. In a preferred embodiment the container 222 comprises a vial. The injector 100 comprises a delivery system 200 (see also FIG. 5) comprised of a vial container sub-assembly (VCSA) 220, a drive control sub-assembly (DCSA) 240, and a flow path sub-assembly (FSA) 260. The delivery system 200 is mounted to and rotational with the carrier 130. An adhesive 102 provided on the base 120 is preferable partially or completely annular and secures the injector 100 to a patient's body. A removable adhesive backing 106 covers an adhesive surface of the adhesive 102 prior to use, with the backing 106 being removed by a user prior to application to the patient's body.

Figure 4B:
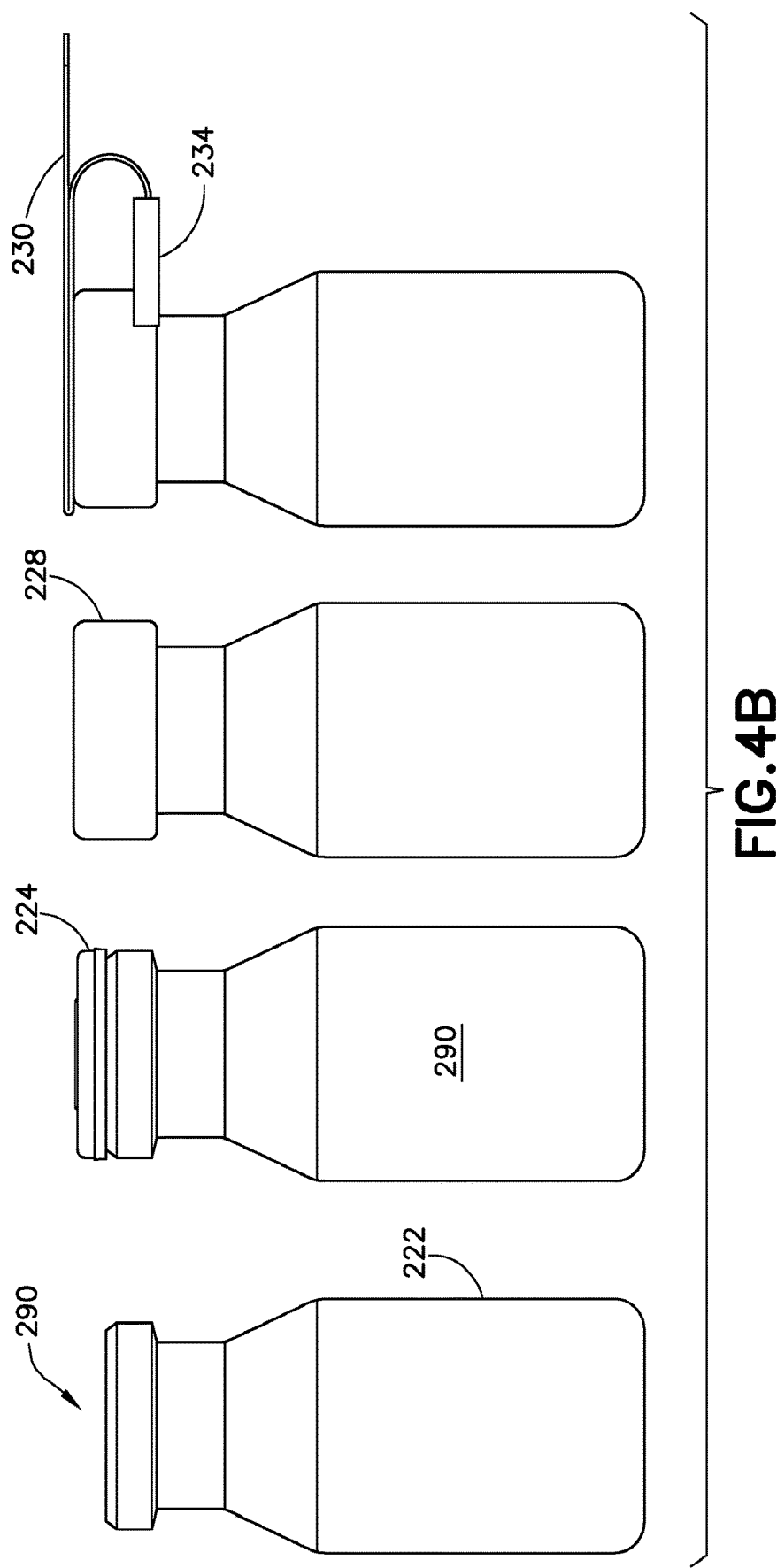
FIG. 4 depicts a vial container sub-assembly (VCSA) in accordance with embodiments of the present invention.

Referring next to FIG. 4 the vial container sub-assembly (VCSA) 220 will be discussed in greater detail. The injector 100 of the present invention contains a primary container 222 for holding a drug 290, preferably a liquid biologic drug. In a preferred embodiment, the primary container 222 is a vial with a septum 224 secured in place over the vial opening by a crimp cap 228. The present invention advantageously uses a standard vial as the primary container 222 which enables use of well-established and accepted filling, sterilization, storage, use, etc., processes for liquid biologic drugs and vials. As depicted in FIG. 4, such a process for filling the vial 222 is depicted in which the drug 290 is introduced into the vial, a septum 224 is sealingly placed over an opening of the vial 222, a crimp cap 228 is crimped in placed to sealingly secure the septum in place, and a sterile barrier tab 230 provided over the exposed septum surface 226. The VCSA 220 is now ready for use in the injector 100 of the present invention. The VCSA 220 leverages well established standard components as well as drug filling and closure techniques which are compatible with existing fill-finish production lines. The sterile barrier tab 230 maintains the sterility of the septum surface 226 during storage. The sterile barrier tab 230 is designed to be removed at the time of use and serves the additional purpose of releasing a container stop 234, enabling a spring-loaded mechanism to establish fluid connection between the VCSA 220 and FSA 260, as described in more detail below.

Figure 6:
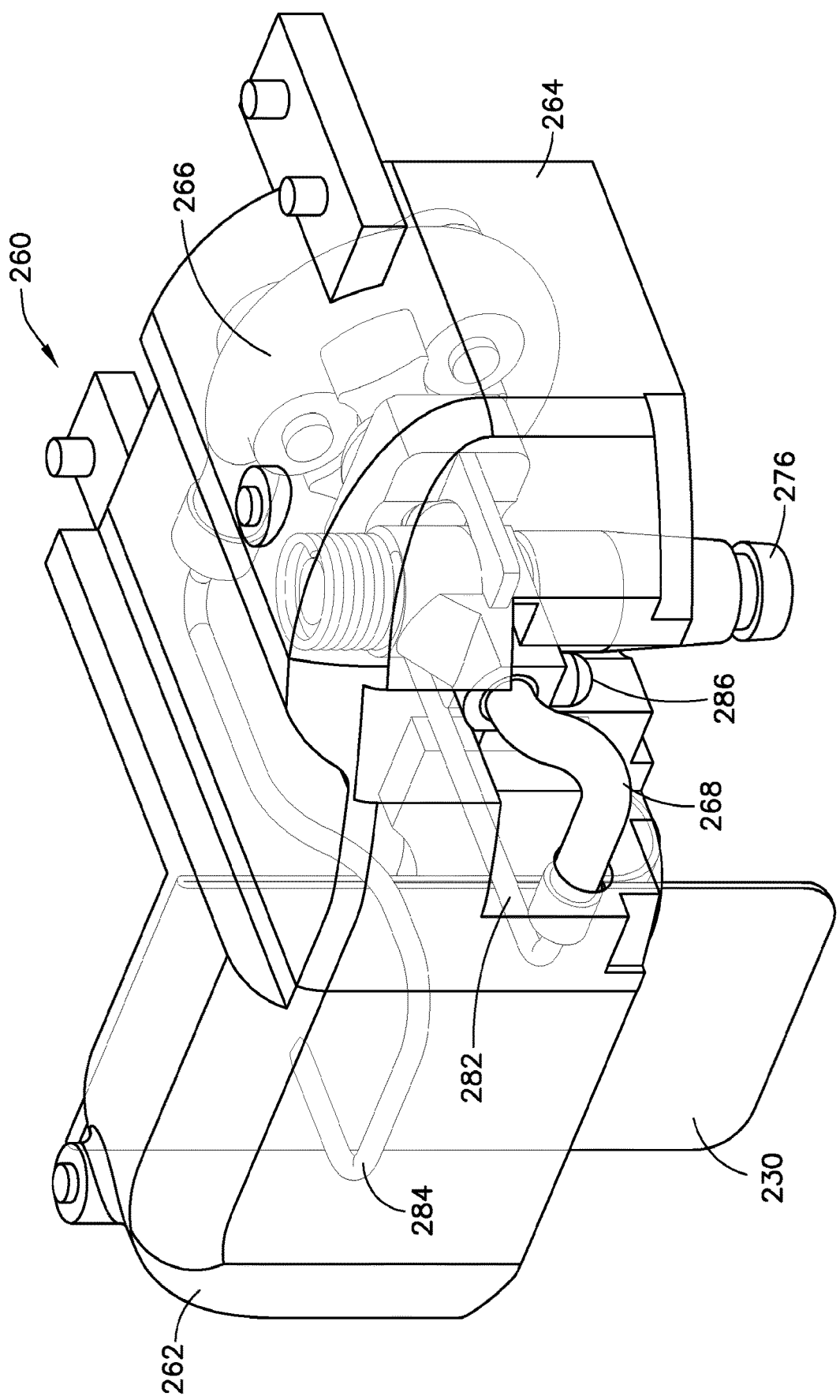
FIG. 6 depicts a flow path sub-assembly (FSA) in accordance with embodiments of the present invention with some parts transparent.

With reference again to FIG. 5 and additional reference to FIG. 6, the FSA 260 comprises a vial access manifold 262, pump transfer block 264, pump tube 266, injection tube 268, and release clip 270. An access needle 284 preferably formed of steel provides a fluid path between the container 222 and the pump tube 266. A fluid may be caused to travel through the access needle 284 and along the fluid path during preparation and use of the inventive injector 100, as described in more detail below. A delivery cannula 282 preferably formed of steel provides a fluid path between the pump tube 266 and an injection needle 278. A fluid may be caused to travel through the delivery cannula 282 and along the fluid path during preparation and use of the inventive injector 100, as described in more detail below. In a preferred embodiment, the access needle 284 and delivery cannula 282 are each at least partially contained in the vial access manifold 262.

The FSA 260 further comprises an injection needle assembly 272 comprising a needle carrier 280 for carrying an injection needle 278, an injection spring 274 for causing the injection needle 278 to move to an injection position, and a needle shield 276 for covering and preferably maintaining the sterility of a sharp, patient end of the injection needle 278 prior to use. The FSA 260 is designed for interface with the VCSA 220 to establish fluid connection between the two sub-assemblies. The FSA 260 design provides a solution which allows its assembly and sterilization to occur separately from the VCSA 220. This allows the vial sterilization and filling processes to remain standardized as opposed to having to introduce a new process that includes attachment of the connecting flow path components as part of the aseptic fill-finish process. Avoiding complexity within aseptic processing is of strategic importance to avoid manufacturing issues when scaling up. Additionally, keeping the FSA 260 separate from the VCSA 220 allows the FSA 260 to be sterilized using gamma sterilization methods, which provide the most economical bulk sterilization method and with fewer limitations on materials that can be used. By being able to go through gamma sterilization, as opposed to other more limiting methods such as Ethylene Oxide (ETO) sterilization, a broader range of materials can be used in the injector 100 as ETO permeability becomes a non-factor. Furthermore, this enables a design of flow passages that may not be sterilizable using ETO, as infiltration of the gas into these hard to reach areas is not a challenge for gamma sterilization. Additionally, the FSA 260 requires no physical contact of pump drive components with the drug. This means that the pump drive mechanisms do not have to be combined with fluid path mechanisms for sterilization. The pump drive mechanisms can be assembled separately and in septic environments without the need for any sterilization. This further simplifies manufacturing processes and keeps the task of validating sterilization processes much more manageable.

With continued reference to FIGS. 5 and 6, the DCSA 240 comprises a stepper drive motor 244 controlled by a controller 400 (see, e.g., FIG. 2) for causing a roller carrier 248 having a plurality of rollers 246 to rotate in first and second directions. Alternatively the drive motor 244 may comprise a DC motor or any other type of motor capable of providing the described functionality. The rotation of the roller carrier 248 in the first and second directions creates a peristaltic pump that causes fluid to move along the fluid path defined by the access needle 284, pump tube 266, delivery cannula 282, injection tube 268 and injection needle 278. In a priming mode, prior to use of the injector 100 and injection of the drug 290, the drive motor 244 causes air to be drawn into the injector 100 via the injection needle 278, and further causes air to move along the fluid path into the container 222, creating a positive pressure in the container 222 with respect to ambient. In a use or injection mode, the drive motor 244 causes the liquid drug 290 to move from the container 222 along the fluid path and exit the injection needle 278 into the patient. The roller carrier 248 may contain any means for multiple and localized contacting with the pump tube 266 to produce peristaltic pumping action, for example, fixed lobes which contact and slide against the pump tube 266, a plurality of rollers 246 which spin freely about spindles of the roller carrier 248 while the rollers 246 roll in contact with the pump tube 266, and quasi-fixed lobes which are integrated features of the roller carrier 248 and slide in contact against the pump tube 266 but experience flexion when under load from static and/or dynamic engagement with the pump tube 266. The pump tube 266 with cross-sectional shape circular but may also be elliptical or other non-circular geometry to enhance resistance against tube kinking during assembly or during operation.

The present invention advantageously recognizes that application of a peristaltic method for administration of biologic drugs is uniquely well-suited for use with an integrated standard vial, as liquid cannot be pushed out (as in syringes or cartridges) and instead must be pulled out of the vial. The interface of the DCSA 240 with the FSA 260 enables the peristaltic pump to pressurize the vial by pulling air into the system first, before reversing to begin fluid extraction and injection into the patient. This aspect of the present invention was inspired by common syringe and vial delivery methods, where an empty syringe is used to fill the vial with a volume of air equal to dose volume to be taken from the vial, before extending the syringe plunger and pulling the drug out of the vial container. The air pulled into the injector 100 system can be from the ambient environment just as has been done for the long practiced syringe and vial method. This process prevents a vacuum from building inside the vial as its contents are extracted which can prevent full extraction of the drug. The injector 100 of the present invention accomplishes this same air pressurization step automatically avoiding the need for an additional vial venting mechanism.

Figure 10A:
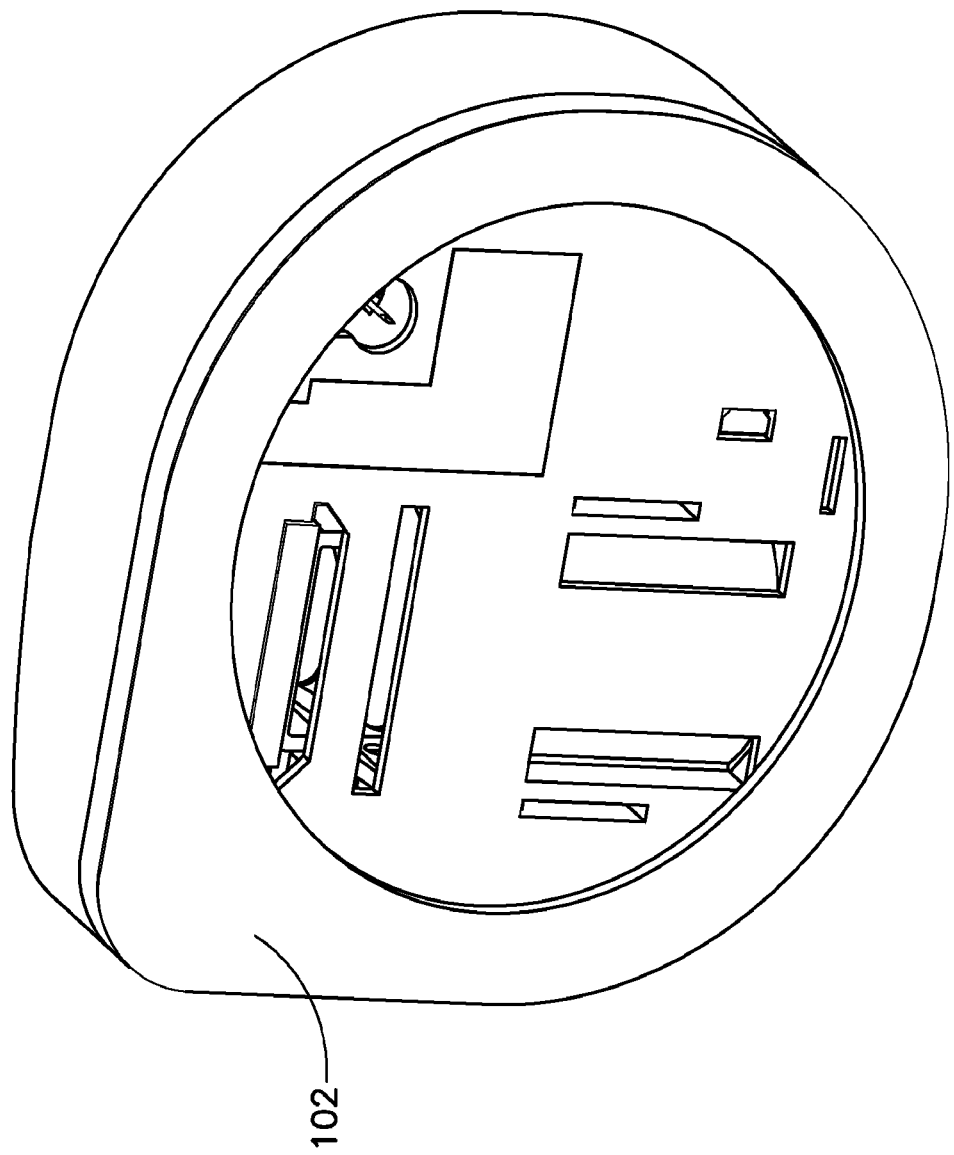
FIGS. 10A-10C depict views of a wearable injector in accordance with embodiments of the present invention in a ready-to-use state.
Figure 10B:
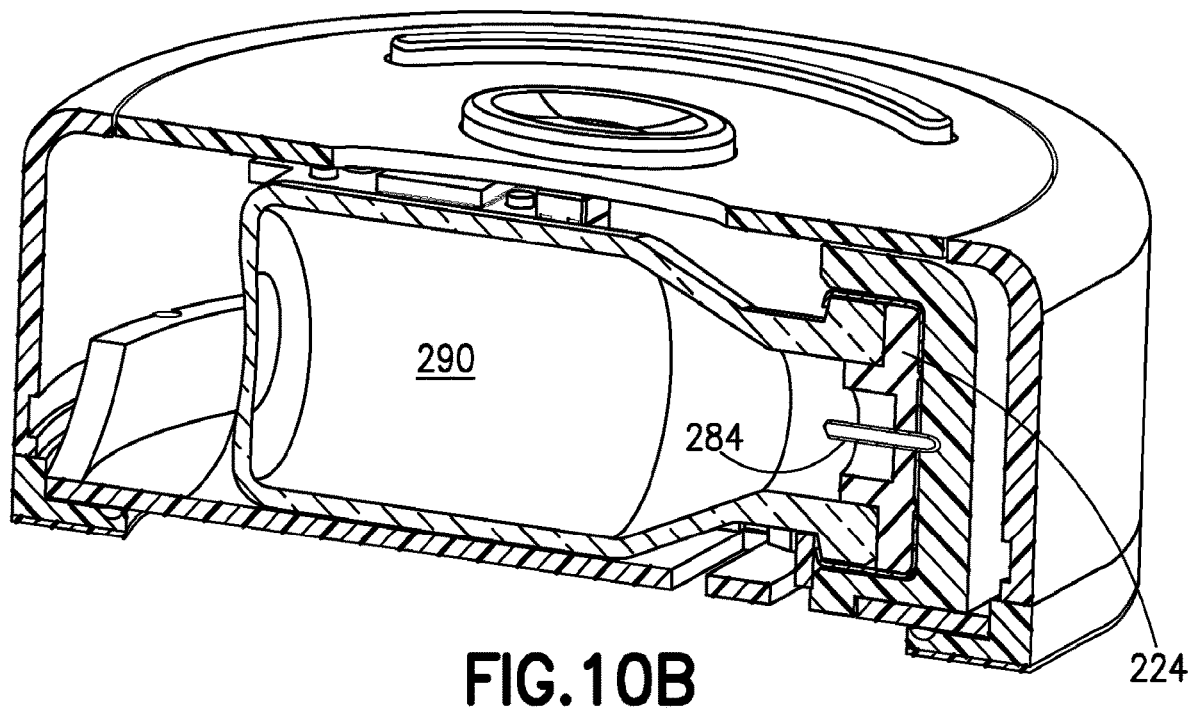
Figure 10C:
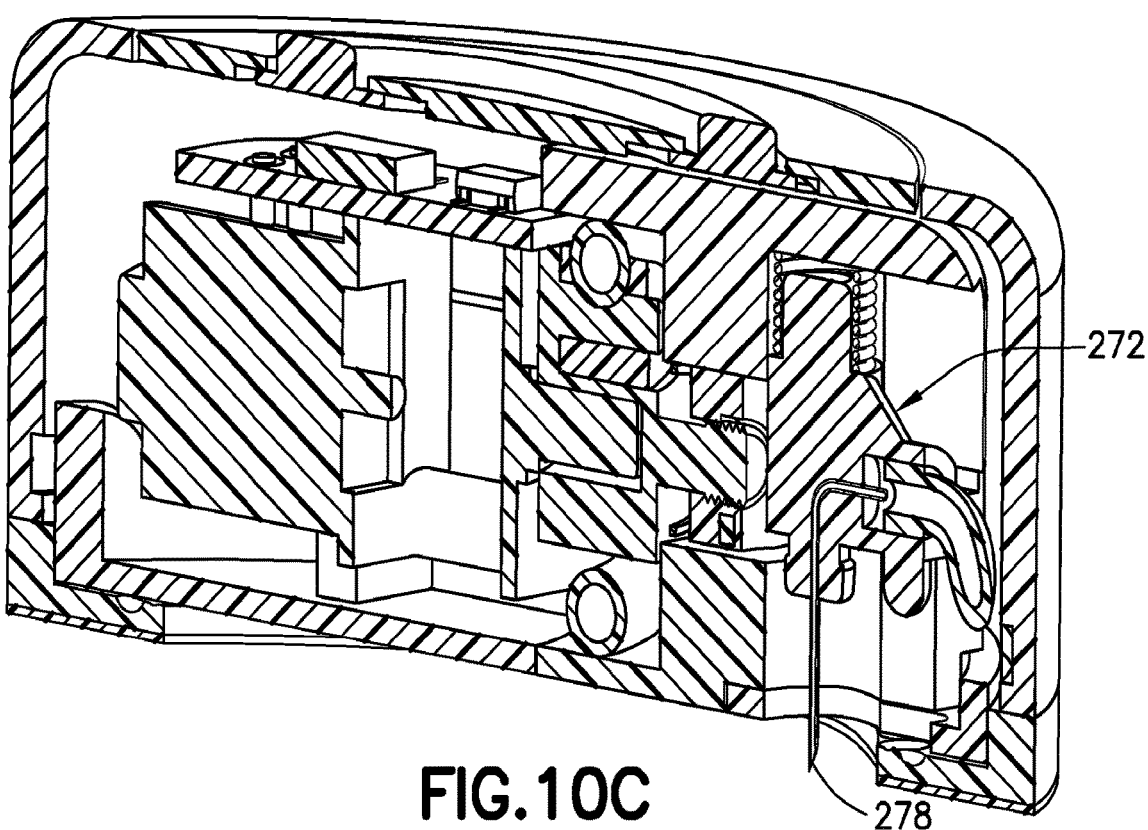
Figure 11A:
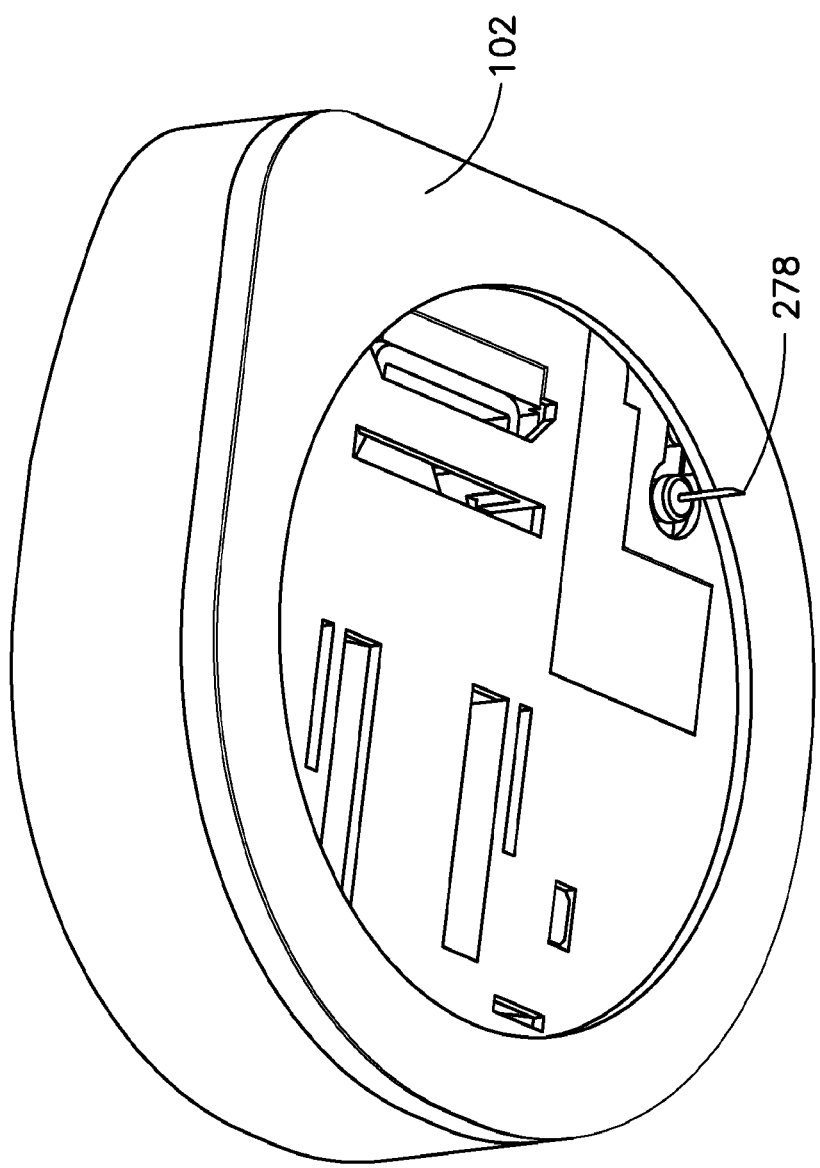
FIGS. 11A-11C depict views of a wearable injector in accordance with embodiments of the present invention in an injection state.
Figure 11B:
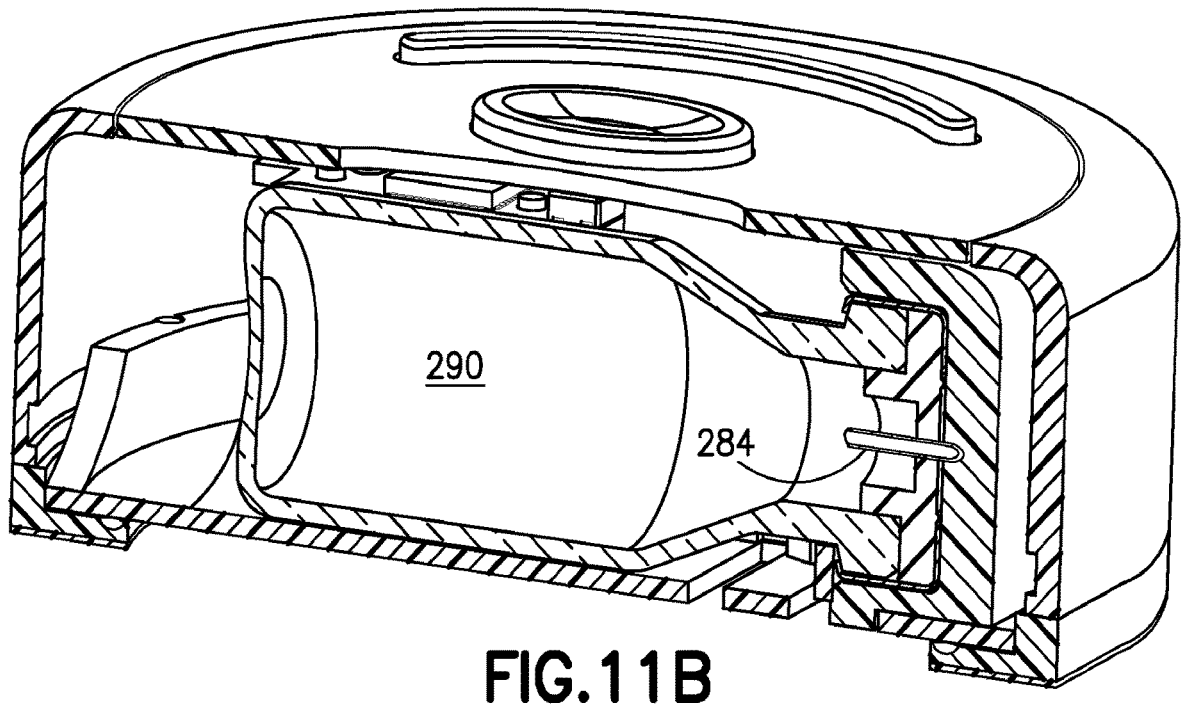
Figure 11C:
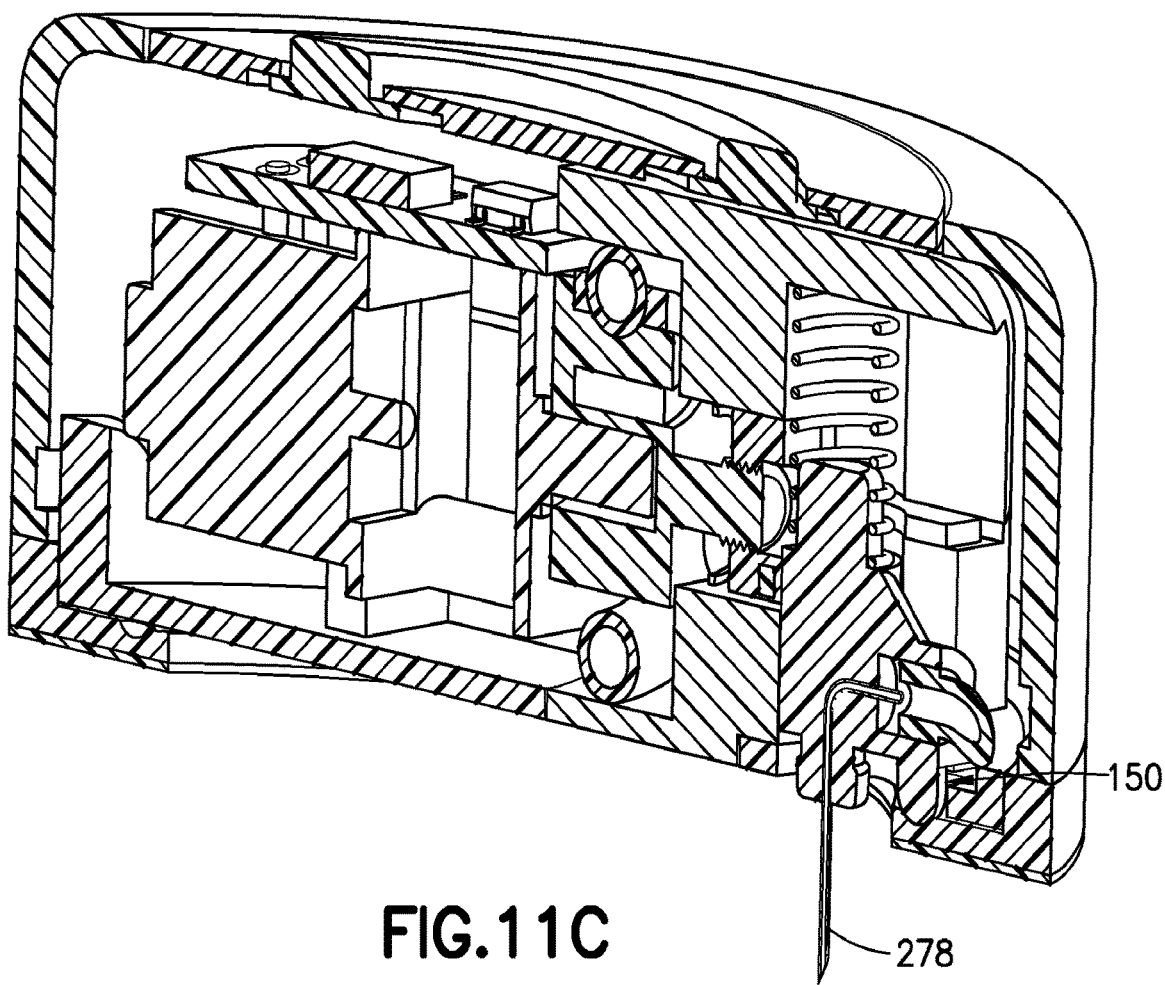

The DCSA 240 not only provides the pumping action, but also the means for releasing the injection needle 278 from a stored position to an injection position, as can be seen in FIGS. 5 and 6 (see also FIGS. 10C and 11C). A release clip 270 has arms 270a, 270b that are sized and shaped to engage a part of the needle carrier 280 and maintain the needle carrier 280 and needle 278 fixed in place prior to use. More importantly, the release clip 270 is controlled by the controller 400 to ensure that the needle carrier 280 and needle 278 are only released, enabling injection of the needle 278 into the patient's skin, when predetermined conditions of the injector 100 are satisfied. The release clip 270 thus locks the needle carrier 280 and needle 278 to prevent untimely or accidental activation.

Control of the release clip 270 by the controller 400 is effected by a plurality of sensors in the injector 100 that monitor spatial orientation of the container 222, temperature of the drug 290 contained within the container 222, and temperature of the base 120, i.e., temperature of the patient at the injection site. After placement on the patient's body, the container 222 must be properly oriented with respect to gravity to allow proper uptake of the liquid drug 290 by the delivery system 200. Or alternatively, the injector 100 may be configured to not permit rotation of the system carrier 130 relative to the housing 110 and base 120, where in such configuration the injector 100 is oriented properly by the user before placement on patient's body. With the needle insertion activated electro-mechanically, the needle can be locked out from activation until proper orientation of the container 222 is detected through integration of an orientation sensor 330 to determine orientation of the container 222. Additionally, it is desirable to allow the drug 290 to warm prior to beginning injection into the patient, which is monitored by a container temperature sensor 320. Through integration of thermal sensors, the injector 100 can be prevented from needle activation and/or commencing of fluid pumping until drug warming has been completed. Furthermore, a body temperature sensor 310 detects when the injector 100 has been placed on the patient's body to further restrict injector activation until properly affixed to a patient's skin.

The controller 400 receives input from at least one of the orientation sensor 330, container temperature sensor 320, and body temperature sensor 310, and controls movement of the release clip 270 by the drive motor 244 through a threaded interface between them via the pump wheel 242. Preferably the drive motor 244 causes the release clip 270 to move in a direction transverse to the longitudinal axis of the injection needle 278 and away from the drive motor 244 to release the injection needle 278. Such movement causes arms 270a, 270b of the release clip 270 to be displaced with respect to the needle carrier 280, thereby presenting an opening to the needle carrier 280, allowing it to be displaced by the insertion spring 274, causing the injection needle 272 to enter the patient's skin.

The threaded engagement between the drive motor 244 and the release clip 270 via the pump wheel 242 allows the rotation of the pump wheel 242 to occur in the direction needed to introduce air into the container 222 without disrupting retention of the injection needle 278. Only once the pump wheel 242 is reversed will the release clip 270 translate forward to release the injection needle 278. Once the injection needle 278 releases, the release clip 270 becomes mechanically decoupled from the pump wheel 242, allowing the pump wheel 242 to continue its rotation to dispense the drug.

The present invention advantageously coordinates a plurality of mechanical systems of the inventive injector 100 so that the retention clip is timed to translate to the point of needle release into the patient only after flow-path priming has completed. A retention clip to pump wheel threaded interface enables air injection via one direction of motor rotation without disrupting needle retention, whereas only upon reversal of the motor does the release clip begin to translate forward to trigger needle insertion into the patient. An integrated wave spring feature of the retention clip provides the necessary mechanical bias for thread engagement between the pump wheel and retention clip to occur upon motor reversal following completion of the air injection step.

Figure 3:
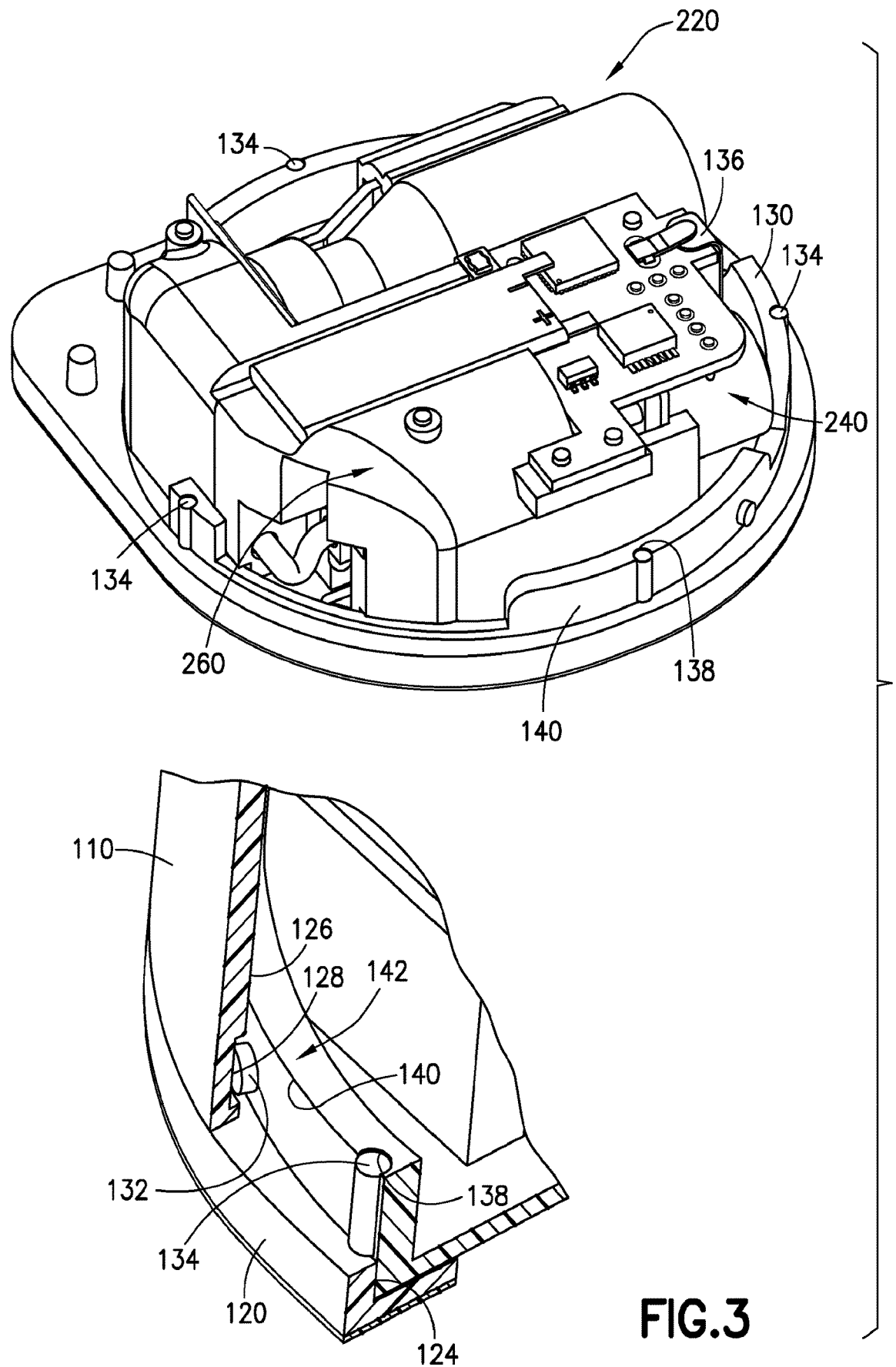
FIG. 3 depicts a view of a wearable injector in accordance with embodiments of the present invention with the housing removed to show certain internal components.
Figure 8A:
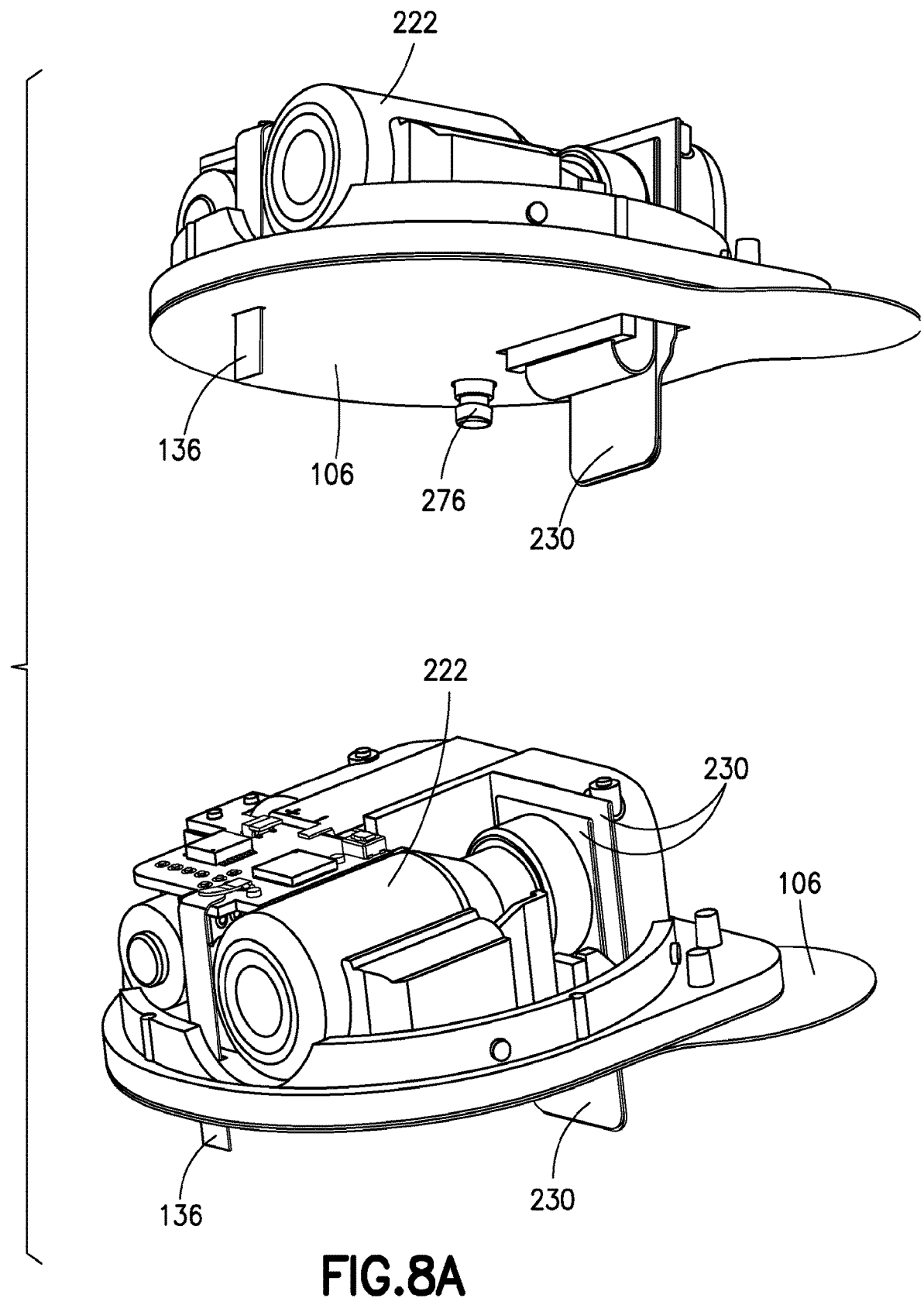
FIG. 8A depicts part of a wearable injector in accordance with embodiments of the present invention in a stored state and with certain parts removed for visibility.

The VCSA 220, FSA 260 and DCSA 240 sub-systems previously described are assembled in, into or on the delivery system carrier 130, as depicted in FIG. 3. The delivery system carrier 130 is sized, shaped and configured to rotate relative to the housing 110 and base 120 to allow the VCSA 220, FSA 260, and DCSA 240 to all rotate together as one unit to properly orient the container 222 for drug delivery. Additionally, the base 120 includes one or more openings for the sterile barrier tab 230 to pass through, see, e.g., FIGS. 9A, 10A and 11A. In a preferred embodiment, the sterile barrier tab 230 comprises two release tabs, as depicted in FIG. 2, one of which provides a sterile barrier for the exposed end of the access needle 284, and the other of which provides a sterile barrier for the exposed surface 226 of the septum 224. A container stop 234 is secured to an end of the septum surface sterile barrier tab 230 that is removed coincident with removal of that sterile barrier tab 230. Removal of the container stop 234 enables the container 222 to be moved causing the exposed sharp tip of the access needle 284 to pierce the septum 224, establishing a fluid path from the container 222 to the injection needle 278. The two sterile barrier tabs 230 are configured such that one removal action peels both tabs triggering fluid connection between the container 222 and the FSA 260. This sequence of functions is intended to occur in rapid succession upon removal of the injector 100 from its secondary packaging, or alternatively upon removal of the adhesive backing 106, such that certain pre-injection steps are completed passively to the user. More specifically, a user removes the injector 100 from its secondary packaging in preparation for use, which may simultaneously remove the sterile barrier tabs 230 and container stop 234. The user next removes the adhesive backing 106 which may simultaneously remove the sterile barrier tabs 230 and container stop 234 (if not achieved during the removal from packaging step) or, alternatively, the adhesive backing 106 and sterile barrier tabs 230 may be removed via discrete, separate actions. In either case, once the container stop 234 is removed, the container 222 is caused to move from its storage position, depicted in FIG. 8A, for example, to its ready position, depicted in FIG. 8B, for example, in which a tip of the access needle 284 pierces the septum 224 connecting the interior chamber of the container 222 with the fluid path. Such movement of the container 222 is caused by a pair of springs 232 provided in channels defined in each side of a container cradle 238, that act upon a vial activator 112 (see, e.g., FIG. 2). Advantageously, the vial activator 112 engages the crimp cap 228 of the VCSA 220 which reduces the stress imposed in the container 222 by the springs 232 and reduces the risk of container breakage.

A further improvement of the present invention is directed to system power-on and priming/arming for injection. The present invention is thus further directed to an injector 100 having a power-on pull tab 136 as an integral part of removing the device from its packaging, or alternatively upon removal of the adhesive backing 106.

Figure 7A:
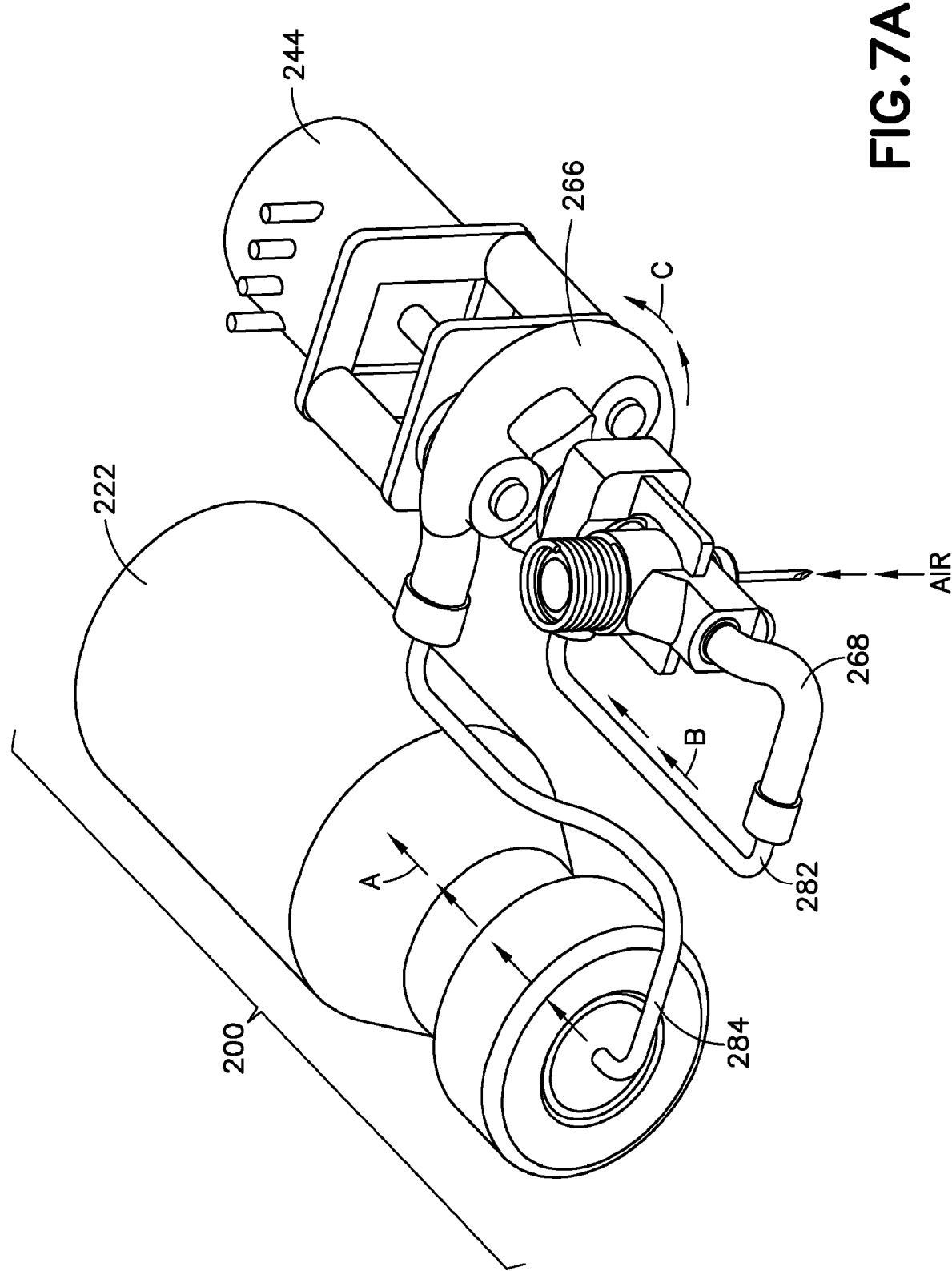
FIGS. 7A and 7B depict a delivery system in accordance with embodiment of the present invention in a priming state and in an injection state.
Figure 7B:
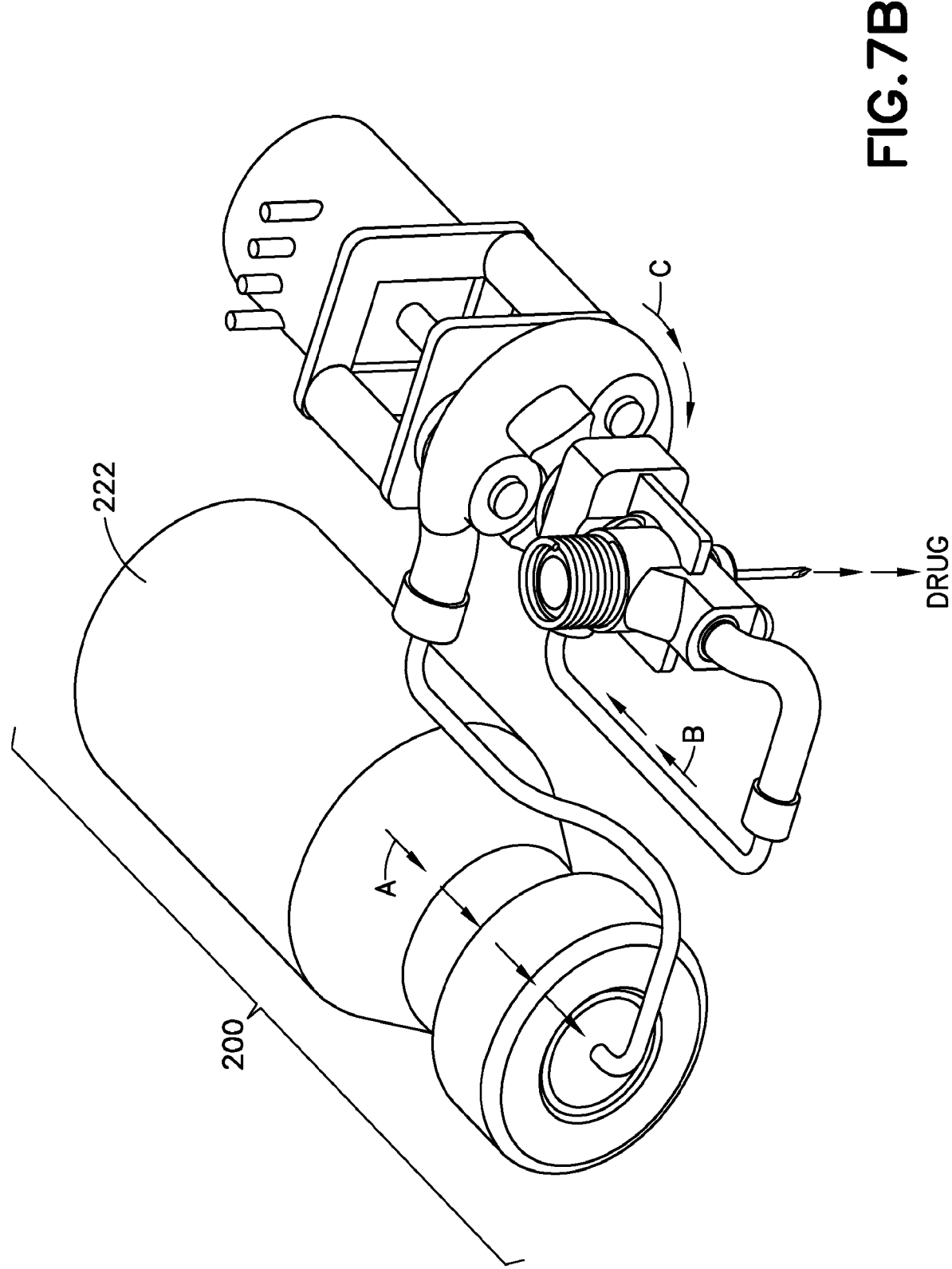

With reference next to FIGS. 3, 7A and 7B, the DCSA 240 and FSA 260 function as a peristaltic pump mechanism capable of injecting air into the container 222 and extracting the drug 290 from the container 222 along the same fluid path. In an air injection or priming state, air injection preferably occurs automatically after injector 100 is powered on by removal of the power-on pull tab 136. Advantageously, the controller 400 enables the injector 100 of the present invention to control the volume of air injected into the container 222 to a pre-set amount that is proportional to volume of drug 290 in the container 222. Preferably, the drive motor 244 causes the pump wheel 242 to rotate in a counter-clockwise direction, as indicated by arrow "C" of FIG. 7A. Such rotation draws air into the needle 278 and causes the air to flow along the fluid path comprised of the access needle 284, pump tube 266, delivery cannula 282, injection tube 268 and injection needle 278, and into the container 222, as indicated by arrows "B" and "A" in FIG. 7A. This step avoids the need for separate venting of the container 222 and overcomes vacuum effects which would otherwise resist fluid extraction from the container 222 by establishing and maintaining upstream positive pressure throughout injection. The inventive injector 100 further provides a system with which, immediately following completion of the air injection step, the injector 100 automatically reverses the drive motor 244 direction (i.e., reverses the pump direction) and begins to prime the fluid path. This continues after the injector 100 is placed on the patient's body and properly oriented to deliver the entire drug volume contained within the container 222.

Figure 8B:
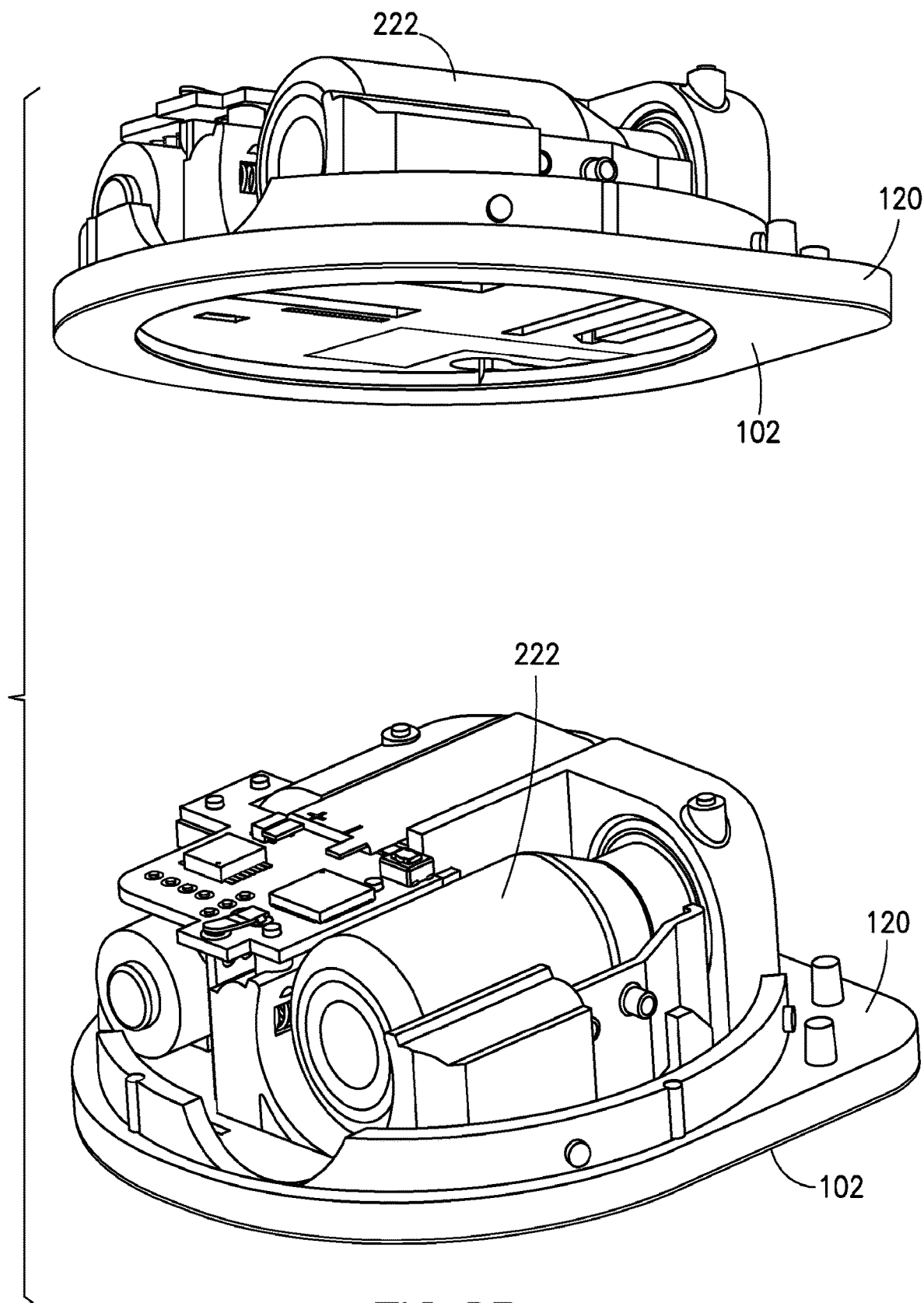
FIG. 8B depicts part of a wearable injector in accordance with embodiments of the present invention in a ready-to-use state and with certain parts removed for visibility.

After placement on body, the present invention is designed and configured to self-orient (FIGS. 1A and 1B) or permit manual orienting (FIGS. 1C and 1D), to position the container 222 into the proper orientation for drug extraction and injection. As depicted in FIGS. 2 and 8B the adhesive 102 is generally annular or partially annular and secures the housing 110 to the patient. Once in place on the patient movement of the injector 100, specifically movement of the housing 110 and the base 120, rotational or otherwise, is prevented by the adhesive 102. The delivery system carrier 130 is contained within the housing 110 but free to rotate with respect thereto until needle activation is triggered at which point the delivery system carrier 130 and housing 110 are locked in position.

Rotation of the delivery system carrier 130 with respect to the housing 110 and base 120 is prevented or permitted based upon certain criteria of the injection device 100, as determined by the controller 400. Such rotation is prevented or permitted by a rotational lockout 150 (see, e.g., FIG. 11C) comprised of a first part defined on the needle carrier 280 as a semi-spherical needle position nub 286 (see, e.g., FIGS. 5 and 6) that is selectively positionable into and out of a second part comprised of any one of a plurality of recesses 122 defined in the base 120 (see, e.g., FIG. 2). The rotational lockout 150 is engaged upon insertion of the injection needle 278 into the patient thereby rotationally locking the delivery system carrier 130 relative to the housing 110 and base 120, thus preventing lateral motion of the needle 278 after insertion into the patient's skin. An orientation sensor 330, preferably an accelerometer, monitors the orientation of the delivery system carrier 130, and consequently the orientation of the container 222 before and after on-body placement. Such monitoring enables the controller 400 to control the rotational lockout 150 to provide means of electromechanical interlocking of FSA 260 (and the needle 278) and the DCSA 240 based upon the orientation of the container 222 such that needle insertion after placement on-body can only occur when the container 222 is properly oriented and such that pumping is only engaged during times when the container 222 is properly oriented.

In addition to the positional control provided by the rotational lockout 150, the orientation sensor 330 also enables the controller 400 to control the drive motor 244 of the DCSA 240 to toggle the DCSA 240 on and off depending upon the orientational position of the injector 100. The present invention thus provides a system capable of on/off pumping toggling where pauses in pumping occurs in response to patient movement if such movement causes moments when the container 222 in not oriented properly or stable. In an embodiment, the controller 400 activates an audible and/or visual signal to alert the patient of the temporary state of improper container orientation.

As previously noted, the delivery system carrier 130 is rotatable within the housing 110 and base 120. The rotation may be user or gravity controlled and can ensure that the container 222 is properly oriented to facilitate delivery of the drug 290. With reference to FIG. 3, rotation of the delivery system carrier 130 is facilitated by a bearing defined by a plurality of rollers 134 disposed between a surface of the delivery system carrier 130 and surfaces of the base 120 and housing 110. Preferably, a plurality of rollers 134 are circumferentially and equidistantly displaced about an outer surface 140 of the delivery system carrier 130. A recess 138 is defined in the outer surface 140 of the delivery system carrier 130 to receive each of the plurality of rollers 134, with the rollers being freely rotatable in the recess 138. A part of each roller 134 engages an inner surface 124 of the base 120, and a part engages an inner surface 126 of the housing 110 acting as a bearing that provides means for the container 222 to self-orient to enable proper uptake and extraction of the drug 290 from the container 222. The rollers 134 thus enable rotational movement of the delivery system carrier 130 with respect to the housing 110 and base 120, facilitating proper positioning of the delivery system carrier 130 and the container 222. A guide 142 comprised of a guide pin 132 defined on the outer surface 140 of the delivery system carrier 130 and a track 128 defined in the inner surface 126 of the housing 110 further facilitates rotational movement of the delivery system carrier 130 and maintains it in a desired position with respect to the housing 110 and base 120. These features of the present invention are directed to container orientation control and pump feedback sensing aspects of the inventive injector 100. The annular or partially annular shape of the adhesive 102 enables the base 140 to still rotate freely after placement of the injector 100 on body, and furthermore to provide a clear unobstructed path for needle insertion into patient tissue.

Figure 9B:
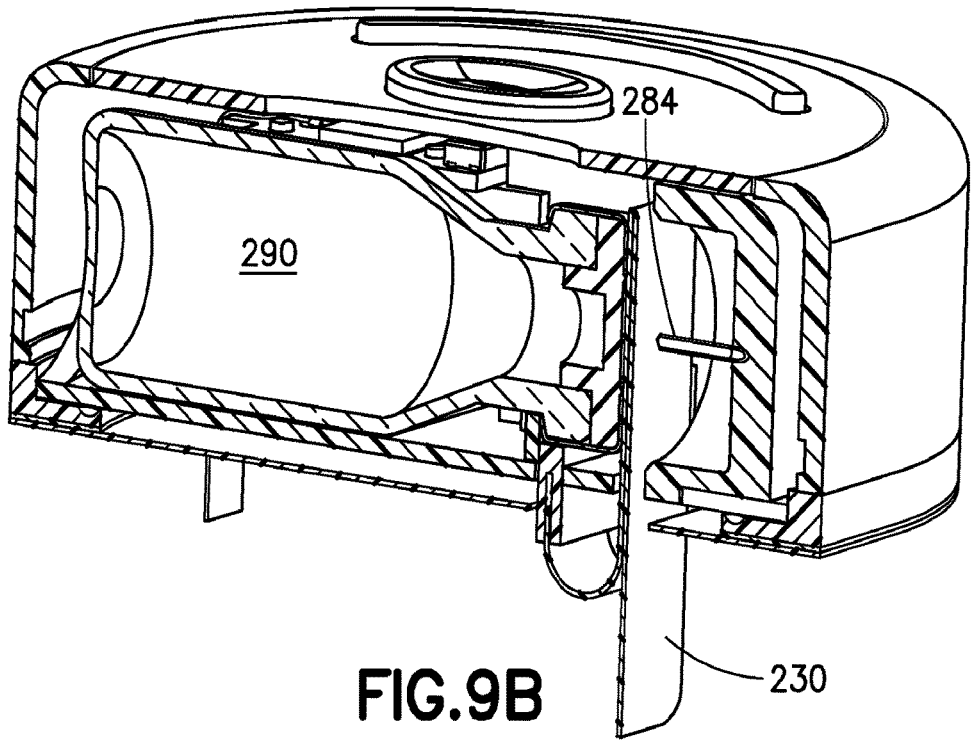
Figure 9C:
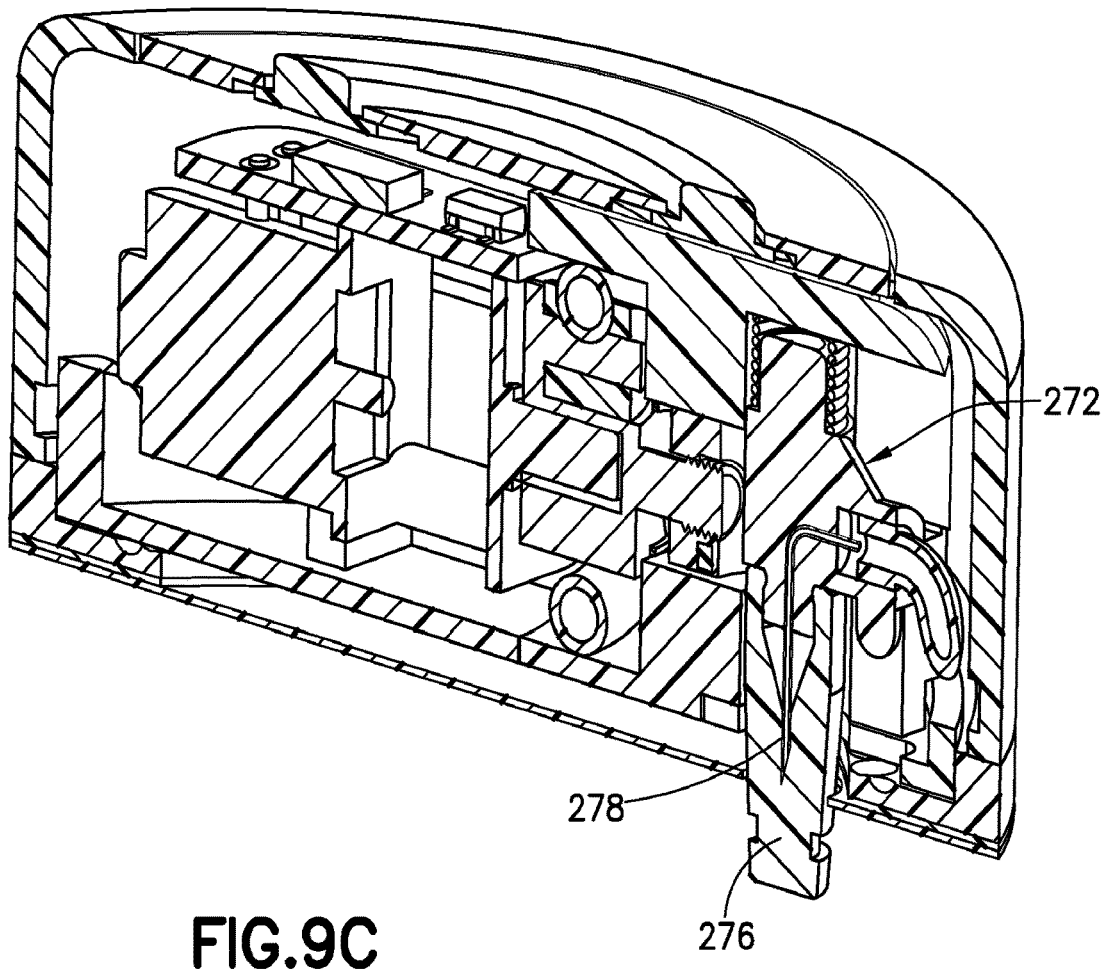

An exemplary, illustrative and non-limiting use of the present invention will now be discussed with reference to FIGS. 9A-9C, 10A-10C and 11A-11C. In general, FIGS. 9A-9C depict the injector 100 of the present invention in a storage state prior to use. This can be the state of the injector 100 when it is contained in its secondary packaging or after it is removed from that packaging. In the stored state the adhesive backing 106, sterile barrier tab 230, power-on pull tab 136 and needle shield 276 are in place. The container 222 is in a first position in which it is not in fluid communication with the fluid path and in which the septum surface 226 and the access needle 284 are each maintained in a sterile state by the presence of the sterile barrier tab 230. The injection needle 278 is also maintained in a sterile state by the needle shield 276.

FIGS. 10A-10C generally depict the inventive injector 100 in a ready to use state but prior to placement on the patient's body. The adhesive backing 106, sterile barrier tab 230, power-on pull tab 136 and needle shield 276 are removed, which can occur simultaneously with removal of the injector 100 from its secondary packaging, or via separate discrete steps carried-out by the user. Removal of the sterile barrier tab 230 also causes removal of the container stop 234, releasing the container 222 for movement in the container cradle 238 by the container drive springs 232 acting upon the container activator 112 (see, e.g., FIG. 2), which acts upon the crimp cap 228. Such movement causes a point tip of the access needle 284 to pierce the septum 224 and fluidly connect the interior chamber of the container 222 with the fluid path. In this state a fluid can be introduced into or extracted from the chamber of the container 222, depending at least in part upon operation of the DCSA 240.

FIGS. 11A-11C generally depict the inventive injector 100 in an injection state that occurs when the injector 100 is in place on the patient's body. In this state the injection needle 278 has pierced the patient's skin, and rotation of the delivery system carrier 130 and injection needle 278 are prevented by the rotation lockout 150 comprised of the needle position nub 286 and at least one recess 122 in the base 120. These conditions occur only upon satisfaction of certain criteria regarding orientation of the container 222, temperature of the drug 290 in the container 222 and presence of the injector 100 on the patient's body.

The In use, a user of the injector 100 of the present invention removes the injector 100 from its secondary packaging such as a blister pack. In an embodiment of the present invention, such removal will also remove the power-on pull tab 136, connecting the battery 402 with the controller 400 and initializing the injector 100. Alternatively, a separate step may be required of the user to remove the power-on pull tab 136. Removal of the injector 100 from the blister pack may also cause removal of the adhesive backing 106, exposing the adhesive 102. In such an embodiment, removal of the injector 100 from the blister pack renders the injector 100 ready to place on the patient's skin and further ready to use. Alternatively, a separate step may be required of the user to remover the adhesive backing 106. Once the injector is removed from its secondary packaging and the power-on pull tab 136 and adhesive backing 106 are removed, the injector 100 is ready for placement on the patient's body and use. Activation of the injector 100 by the controller 400 depends upon the signals received by the controller 400 from the body temperature sensor 310, container temperature sensor 320 and orientation sensor 330. The body temperature sensor 310 is able to determine if the injector 100 is on body by detecting a temperature rising, and eventually reaching, the range of human body temperature (or other animal body temperature). Only when the injector 100 is on body will the body temperature sensor 310 send an activation signal to the controller 400. The container temperature sensor 320 can determine the temperature of the drug 290 in the container 222 to ensure that it is within a desired temperature range before the injector 100 begins an injection. Certain drugs are stored refrigerated and thus benefit from being brought to a warmer temperature before they are injected. The container temperature sensor 320 sends a signal to the controller 400 when the sensor 320 detects that the temperature of the drug 290 is at a desired level or within a desired range. The orientation sensor 330 determines the position of the container 222 with respect to a predetermined desired position that facilitates operation of the injector 100 to ensure proper and complete delivery of the drug 290. As noted, the delivery system carrier 130 can be configured to auto-orient, or for user orientation. In both cases a light bar 114 in the housing 110 indicates when the delivery system carrier 130 is properly oriented. The orientation sensor 330 sends a signal to the controller 400 when the delivery system carrier 130 is properly oriented.

Figure 12:
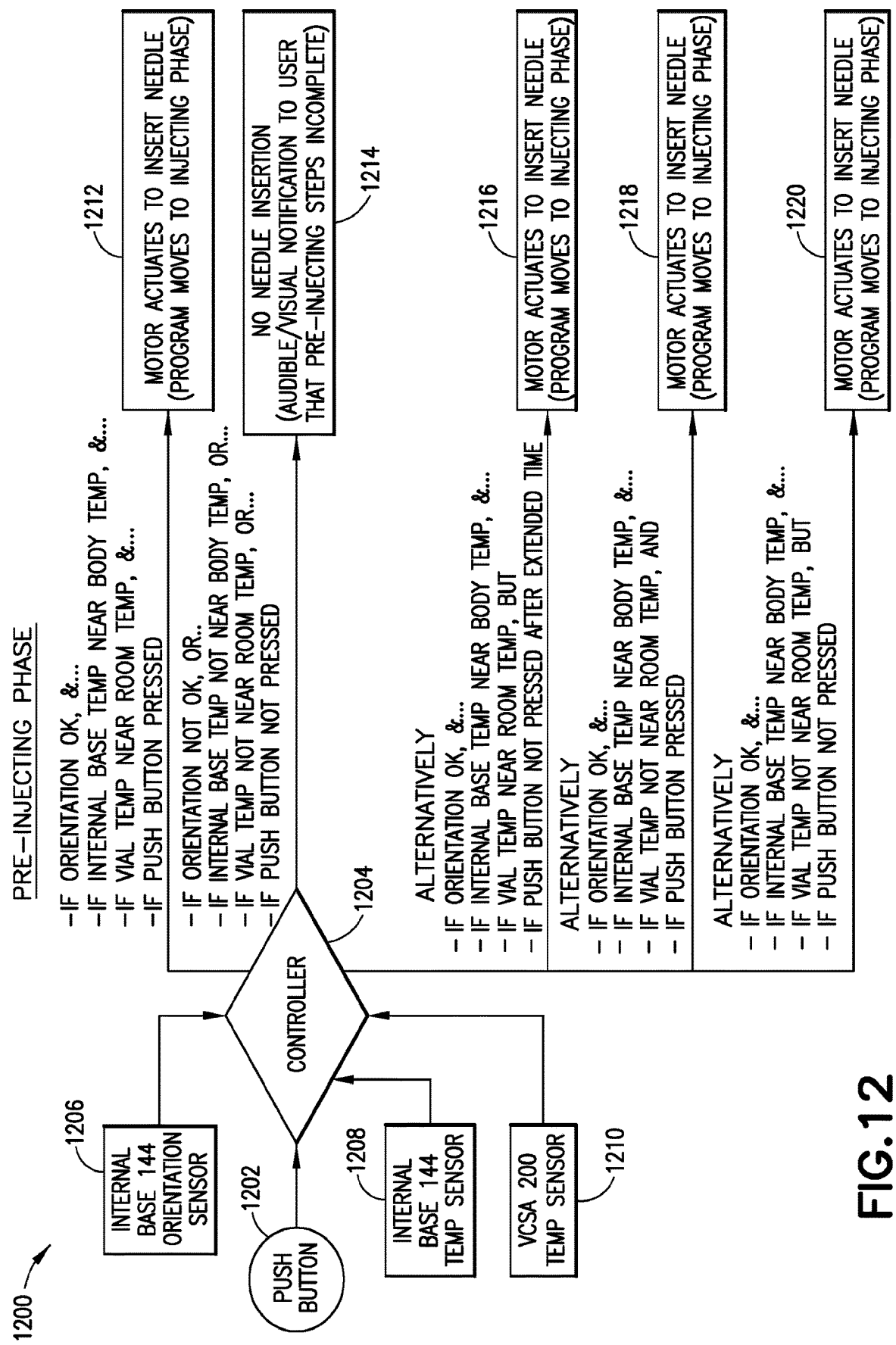
FIG. 12 depicts a flow diagram of a pre-injecting phase of a wearable injector in accordance with embodiments of the present invention.
Figure 13:
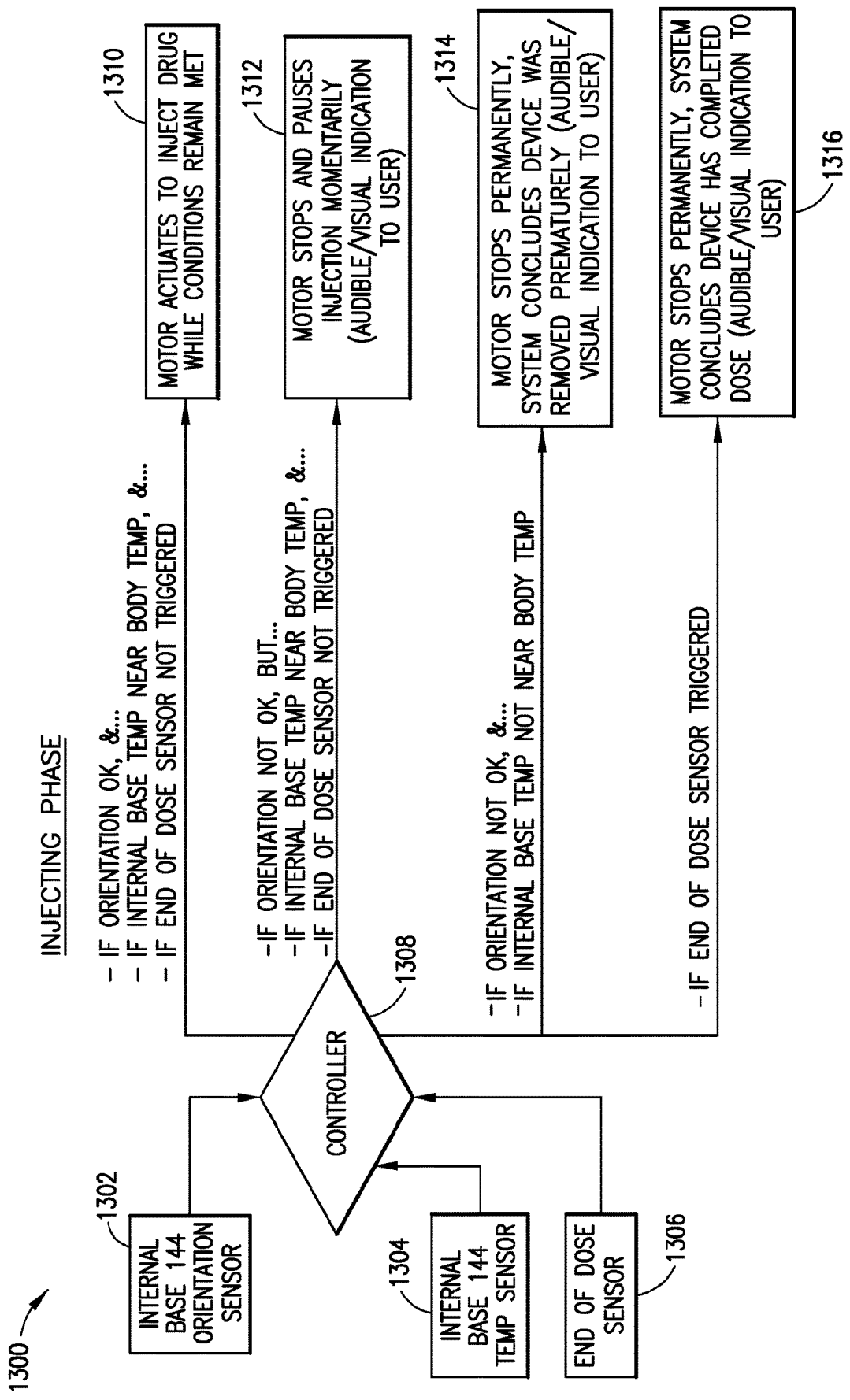
FIG. 13 depicts a flow diagram of an injecting phase of a wearable injector in accordance with embodiments of the present invention.

Referring next to FIGS. 12 and 13, certain aspects of the present invention and its operation will now be discussed in greater detail. FIG. 12 discloses certain steps carried-out by the controller 400 in a pre-injecting or pre-injection phase of operation of the injector 100 of the present invention. For this phase the controller 400 receives input from at least the orientation sensor 330 at 1206, the body temperature sensor 310 at 1208, and container temperature sensor 320 at 1210. These sensors monitor and detect various conditions of the injector 100, the drug 290 contained in the container 222, and the patient, as illustrative, non-limiting examples, to ensure that the injector 100 is activated only under certain conditions, e.g., temperature and orientational. The controller 400 enables operation of the injector 100 (at 1204) based upon the orientation of the injector 100, patient's body temperature, and temperature of the drug to be injected.

The orientation sensor 330 detects and determines the orientation of the delivery system carrier 130, as its orientation is important to ensure proper operation of the injector 100 and delivery of the drug 290.

The body temperature sensor 310 detects the patient's body temperature to determine when the injector 100 is on-body. The way in which it is concluded that the device has been placed on the patient's body from a temperature sensor may not alone, or at all, be based on reaching a preset temperature level. The best way is likely to monitor the rate of temperature rise to differentiate between a rise due to the device sitting within a room temperature environment versus it being placed on the patient's body, with the rate of rise being much steeper for the latter. The rate of rise in addition to the temperature magnitude may both be needed where a temperature level within 5 degrees F. of human body temperature would be sufficient. In terms of accuracy of the sensor, +/−2 degrees F. with 0.5 degree resolution is preferable.

The container temperature sensor 320 detects the temperature of the container 222 (and drug 290) to determine whether it is near room temperature. It is preferred that drugs reach room temperature before injection. In a preferred embodiment, a drug temperature around 60 degrees F. should be the minimum temperature of the drug before the injector 100 will initiate an injection. Given the drug will still be able to be injected and work properly even if injected colder, significant tolerance is acceptable in terms of the temperature of the drug and room temperature, with accuracy and resolution needed no tighter than as indicated for the on-body detection.

To further activate the injector 100, a user/patient presses a push-button 104, at 1202.

Thereafter, there are five possible outcomes of the pre-injecting phase in accordance with embodiments of the present invention, as indicated by references 1212, 1214, 1216, 1218 and 1220 of FIG. 12. A first outcome, indicated by 1212, occurs when the orientation sensor 330, body temperature sensor 310 and container temperature sensor 320 all detect levels or values that are within their respective predetermined values or ranges. Under these conditions and upon depression of the push-button 104, the controller 400 causes the drive motor 244 to actuate the needle 278 to insert into the patient's skin. The controller 400 then causes the injector 100 to operate in the injection or injecting phase, as depicted in FIG. 13 and discussed below.

A second outcome, indicated by 1214, occurs when the orientation sensor 330 and body temperature sensor 310 each determine that the orientation and temperature of the delivery system carrier 130 are not at their respective predetermined values, the container temperature sensor 320 determines that the container temperature is not at or near room temperature, and the push-button 104 is not pressed. Under these conditions the controller 400 does not cause the drive motor 244 to activate the needle assembly 272, and an audible and/or visual indicator indicates that pre-injection steps have not completed and the injector 100 will not inject.

A third outcome, indicated by 1216, occurs when the orientation sensor 330, body temperature sensor 310 and container temperature sensor 320 all detect levels or values that are within their respective predetermined values or ranges but the push-button 104 is not pressed after a predetermined amount of time. Under these conditions the controller 400 causes the drive motor 244 to actuate the needle assembly 272 to insert the needle into the patient's skin. The controller 400 then causes the injector 100 to operate in the injection or injecting phase, as depicted in FIG. 13 and discussed below.

A fourth outcome, indicated by 1218, occurs when the orientation sensor 330 and body temperature sensor 310 each detect levels or values that are within their respective predetermined values or ranges, but the container temperature sensor 320 does not. Under these conditions and upon depression of the push-button 104, the controller 400 causes the drive motor 244 to actuate the needle assembly 272 to insert into the patient's skin. The controller 400 then causes the injector 100 to operate in the injection or injecting phase, as depicted in FIG. 13 and discussed below.

A fifth outcome, indicated by 1220, occurs when the orientation sensor 330 and body temperature sensor 310 each detect levels or values that are within their respective predetermined values or ranges, but the container temperature sensor 320 does not, and the push-button 104 is not pressed after a predetermined amount of time. Under these conditions the controller 400 causes the drive motor 244 to actuate the needle assembly 272 to insert the needle into the patient's skin. The controller 400 then causes the injector 100 to operate in the injection or injecting phase, as depicted in FIG. 13 and discussed below.

Referring next to FIG. 13, an injection or injecting phase of the injector 100 of the present invention will now be discussed in greater detail. For this phase the controller 400 receives input from at least the orientation sensor 330 at 1302, the body temperature sensor 310 at 1304, and an end of dose sensing at 1306. End of dose sensing is provided by logic programmed into the controller 400 that enables monitoring drive motor 244 current draw such a current draw drop to a predetermined level resulting from the mechanical resistance experienced by the drive motor 244 being reduced indicates that no more liquid is being pumped. Thus end of dose sensing is done indirectly and is part of the logic programmed into the controller 400. These sensors monitor and detect various conditions of the injector 100, the drug 290 contained in the container 222, and the patient, as illustrative, non-limiting examples, to ensure that the injector 100 is activated only under certain conditions, e.g., temperature and orientational, and that the injector 100 stops injecting once the container 222 is empty. The controller 400 enables operation of the injector 100 (at 1308) based upon the orientation of the injector 100, patient's body temperature, and temperature of the drug to be injected.

The orientation sensor 330 detects and determines the orientation of the delivery system carrier 130, as its orientation is important to ensure proper operation of the injector 100 and delivery of the drug 290.

The body temperature sensor 310 detects the patient's body temperature to determine whether the internal base temperature is near the patient's body temperature. The way in which it is concluded that the device has been placed on body from a temperature sensor may not alone, or at all, be based on reaching a preset temperature level. The best way is likely to monitor the rate of temperature rise to differentiate between a rise due to the device sitting within a room temperature environment versus it being placed on the patient's body, with the rate of rise being much steeper for the latter. The rate of rise in addition to the temperature magnitude may both be needed where a temperature level within 5 degrees F. of human body temperature would be sufficient. In terms of accuracy of the sensor, +/−2 degrees F. with 0.5 degree resolution should suffice.

The end of dose sensor 340 detects and determines when delivery of the drug 290 is complete.

Four possible outcomes of the injecting phase are provided in accordance with embodiments of the present invention, as indicated by references 1310, 1312, 1314 and 1316 of FIG. 13. A first outcome, indicated by 1310, occurs when the orientation sensor 330 and body temperature sensor 310 each detect levels or values that are within their respective predetermined values or ranges, and the end of dose sensor 340 does not indicate that delivery of the drug 290 is complete. Under these conditions the drive motor 244 will activate injection of the drug 290 from the container 222, through the needle 278 and into the patient until the end of dose sensor 340 indicates completion of delivery of the drug 290.

A second outcome, indicated by 1312, occurs when the orientation sensor 330 determines that the orientation of the delivery system carrier 130 is not at its predetermined value, but the body temperature sensor 310 indicates that the internal base temperature is. Provided the end of dose sensor 340 has not indicated an end of dose condition, the controller 400 will cause the drive motor 244 to pause injection of the drug 290, preferably also providing an audible and/or visual indicator, until the orientation sensor 330 detects that the delivery system carrier 130 is properly oriented, at which time the controller 400 will cause the drive motor 244 to resume the injection until the end of dose indicator 340 indicates that delivery of the drug 290 is complete.

A third outcome, indicated by 1314, occurs when the orientation sensor 330 determines that the orientation of the delivery system carrier 130 is not at its predetermined value and the body temperature sensor 310 determines that the internal base temperature is not at its predetermined value. The controller 400 interprets these conditions as an indication that the injector 100 has been removed from the patient's skin, and permanently stops delivery of the drug 290. The controller 400 also preferably provides an audible and/or visual indicator of this condition.

A fourth outcome, indicated by 1316, occurs when the end of dose sensor 340 indicates to the controller 400 the delivery of the drug 290 is complete. The controller 400 causes the drive motor 244 to stop and provides an audible and/or visual indicator that delivery of the drug 290 is complete.

Modifications to embodiments of the present invention are possible without departing from the scope of the invention as defined by the accompanying claims. Expressions such as "including," "comprising," "incorporating," "consisting of," "have," "is," used to describe and claim the present invention are intended to be construed in a non-exclusive manner, namely allowing for articles, components or elements not explicitly described herein also to be present. Reference to the singular is to be construed to relate to the plural, where applicable.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A wearable injector for delivering a drug into a body part of a patient comprising:
    a housing;
    a base connected with the housing and releasably securable on the body part of the patient;
    a carrier rotatably arranged within the housing and the base; and
    a delivery system on the carrier comprising:
        a container sub-assembly for containing the drug;
        a drive control sub-assembly coupled with the container sub-assembly and configured for controlling delivery of the drug into the patient;
        flow-path sub-assembly providing a fluid path with the container sub-assembly via which a fluid can be introduced into the container sub-assembly and via which the drug can be extracted from the container sub-assembly, wherein the drive control sub-assembly engages the flow-bath sub-assembly to cause the fluid to be introduced into the container sub-assembly and to cause the drug to be extracted from the container and delivered into the patient;
        a sensor for detecting one of temperature of the body part, temperature of the drug in the container sub-assembly, and orientation of the container sub-assembly; and
        a controller receiving an input from the sensor and controlling the drive control sub-assembly based upon the input to set a state of the injector.

2. A wearable injector according to claim 1, wherein the drive control sub-assembly further comprises a peristaltic pump.

3. A wearable injector according to claim 2, wherein the peristaltic pump further comprises a drive motor and a pump wheel controllable by the drive motor.

4. A wearable injector according to claim 1, wherein the controller receives power from a power source and wherein the container sub-assembly further comprises a container for containing the drug, wherein the controller activates the drive control sub-assembly to pressurize the container when the controller receives power from the power source.

5. A wearable injector according to claim 4, wherein the controller activates the drive control sub-assembly to introduce air into the container via the flow-path sub-assembly when the controller receives power from the power source.

6. A wearable injector according to claim 5, wherein the controller activates the drive control sub-assembly to introduce a predetermined amount of air into the container.

7. A wearable injector according to claim 6, wherein the predetermined amount of air is based upon one of the following (a) and (b): (a) volume of drug to be dispensed, and (b) viscosity of the drug.

8. A wearable injector according to claim 1, wherein the container sub-assembly further comprises a container, and wherein the flow-path sub-assembly defines a fluid path with the container, wherein the drive control sub-assembly causes the injector to be primed by causing air to travel along the fluid path into the container, and wherein the drive control sub-assembly causes the injector to be extracted from the container for delivery into the patient by causing the drug to travel along the fluid path out of the container.

9. A wearable injector according to claim 8, wherein the drive control sub-assembly causes the fluid path to be primed with the drug prior to delivery of the drug into the patient.

10. A wearable injector according to claim 1, wherein the container sub-assembly further comprises a container, and wherein the flow-path sub-assembly defines a fluid path with the container, wherein the drive control sub-assembly causes the injector to be primed by causing air to travel along the fluid path into the container.

11. A wearable injector according to claim 9, wherein the flow-path sub-assembly further comprises an injection needle connected with the fluid path for delivering the drug into the patient, and wherein the drive control sub-assembly causes the drug to travel along the fluid path and through the injection needle into the patient when the injector is primed.

12. A wearable injector according to claim 1, further comprising a bearing between the carrier and housing to at least partially enable rotation of the carrier within the housing.

13. A wearable injector according to claim 12, wherein the bearing comprises at least one roller disposed in a recess defined in one of the carrier and the housing, the roller being freely rotatable in the recess.

14. A wearable injector according to claim 1, further comprising an adhesive on a part of the base to releasably secure the base on the body part of the patient.

15. A wearable injector according to claim 14, wherein the adhesive comprises an annulus or partial annulus on a part of the base.

16. A wearable injector according to claim 1, wherein the container sub-assembly further comprises a container for the drug, and wherein the sensor further comprises an orientation sensor configured to determine an orientation of the container, the controller setting the state of the injector based up the orientation of the container.

17. A wearable injector according to claim 16, wherein the state of the injector comprises one of an injection state and a non-injection state, and wherein the controller is configured to toggle the state of the injector to the injection state from the non-injection state and from the injection state to the non-injection state based upon an output from the orientation sensor.

18. A wearable injector according to claim 1, wherein the container sub-assembly further comprises a container for the drug, and wherein the sensor further comprises a first temperature sensor configured to determine a temperature of the drug in the container, wherein the controller is configured to control the drive control sub-assembly to cause the drug to be delivered into the patient when the temperature of the drug in the container is at least at a predetermined temperature.

19. A wearable injector according to claim 18, wherein the predetermined temperature is at least 60° F.

20. A wearable injector according to claim 1, wherein the container sub-assembly further comprises a container for the drug, and wherein the sensor further comprises a second temperature sensor configured to determine whether the injector is on the patient's body.

21. A wearable injector according to claim 20, wherein the second temperature sensor is configured to determine a temperature of the patient at or near the body part, wherein the controller is configured to control the drive control sub-assembly to cause the drug to be delivered into the patient when the temperature of the patient at or near the body part is at least at a predetermined temperature.

22. A wearable injector according to claim 21, wherein the predetermined temperature is at least within 5° F. of 98.6° F.

23. A wearable injector according to claim 1, further comprising a lock for preventing rotation of the carrier.

24. A wearable injector according to claim 23, wherein the flow-path sub-assembly further comprises an injection needle assembly comprising a needle carrier, an injection needle, and a needle position nub, and wherein the base further comprises at least one recess for receiving the needle position nub, wherein the injection needle assembly is movable from a first position in which the needle position nub and the recess are in spaced apart relation to each other, and a second position in which the needle position nub is in the recess thereby preventing rotation of the carrier.

25. A wearable injector according to claim 1, wherein the container sub-assembly further comprises a container for containing the drug, the container having a pierceable seal, and wherein the flow-path sub-assembly further comprises a fluid path having a needle, the injector further comprising a spring for causing the container to move in a predetermined direction, and a removable barrier located between the pierceable seal and the needle maintain each in a sterile condition, wherein removal of the removable barrier causes the spring to cause the container to move in the predetermined direction in which the needle pierces the pierceable seal.

26. A wearable injector according to claim 25, wherein the injector is contained in a disposable package openable by a user of the injector, wherein the removable barrier is removed coincident with a user opening the package.

27. A wearable injector according to claim 25, further comprising a collar on the container and a container activator, wherein the spring engages the container activator to engage the collar to cause the container to move in a predetermined direction in which the needle pierces the pierceable seal.

28. A wearable injector according to claim 1, further comprising a power source for powering the injector, and a pull-tab that, when pulled enables the power source to power the injector.

29. A wearable injector according to claim 1, wherein the container sub-assembly further comprises a container for containing the drug, and wherein the drive control sub-assembly further comprises a pump operable to pressurize the container, and operable to cause the drug to flow from the container, upon the container being pressurized by the pump to a predetermined level, the pump automatically causes the drug to flow from the container.

30. A wearable injector according to claim 1, further comprising an audible and/or visual indicator indicating a state of the injector.

31. A wearable injector according to claim 30, wherein the state is one of orientation and operational state of the injector.

32. A wearable injector according 10 claim 1, further comprising a push-button for user activation of the injector.

33. A wearable injector according to claim 1, further comprising a needle for delivering the drug into the patient, and wherein the container sub-assembly further comprises a container having a preferred orientation, wherein the carrier is configured to automatically orient the container in the preferred orientation, and wherein the injector is configured to automatically cause the needle to be inserted into the body part of the patient when the container is in the preferred orientation.

34. A wearable injector according to claim 1, further comprising a needle for delivering the drug into the patient and a user-depressible push-button, and wherein the container sub-assembly further comprises a container having a preferred orientation, wherein the carrier is configured to orient the container in the preferred orientation upon user first depression of the push-button, and wherein the injector is configured to cause the needle to be inserted into the body part of the patient when the container is in the preferred orientation upon user subsequent depression of the push-button.

35. A wearable injector according to claim 1, wherein the container sub-assembly further comprises a container having a preferred orientation, the injector further comprising a needle for delivering the drug into the patient and orientation means for changing the orientation of the container, wherein the container orientation is set by user use of the orientation means, and wherein the injector is configured to automatically cause the needle to be inserted into the body part of the patient when the container is in the preferred orientation by user use of the orientation means.

36. A wearable injector according to claim 35, wherein the orientation means comprises a tab connected with the carrier and that enables a user to cause the carrier to rotate within the housing.

37. A wearable injector according to claim 1, further comprising a needle for delivering the drug into the patient, orientation means for changing the orientation of the container, and a user-depressible push-button, wherein the container sub-assembly further comprises a container having a preferred orientation, wherein the container orientation is set by user use of the orientation means subsequent to user first depression of the push-button, and wherein the injector is configured to cause the needle to be inserted into the body part of the patient when the container is in the preferred orientation upon user subsequent depression of the push-button.

38. A wearable injector according to claim 37, wherein the orientation means comprises a tab connected with the carrier and that enables a user to cause the carrier to rotate within the housing.

39. A method for operating a wearable injector comprising a housing, a base connected with the housing and releasably securable on the body part of the patient, a carrier rotatably arranged within the housing and the base, and a delivery system on the carrier comprising a container sub-assembly for containing the drug, a drive control sub-assembly coupled with the container sub-assembly and configured for controlling delivery of the drug into the patient, a flow-path sub-assembly providing a fluid path with the container sub-assembly via which a fluid can be introduced into the container sub-assembly and via which the drug can be extracted from the container sub-assembly, a sensor for detecting one of temperature of the body part, temperature of the drug in the container sub-assembly, and orientation of the container sub-assembly, and a controller receiving an input from the sensor, the method comprising the step of causing the drive control sub-assembly to engage the flow-path sub-assembly to cause the fluid to be introduced into the container sub-assembly and to cause the drug to be extracted from the container and delivered into the patient based upon the input from the sensor to set a state of the injector.

* * * * *